US 9,506,906 B2

(12) United States Patent
Yamashita et al.

(10) Patent No.: US 9,506,906 B2
(45) Date of Patent: Nov. 29, 2016

(54) URINE COMPONENT ANALYSIS DEVICE AND URINE COMPONENT ANALYSIS METHOD

(71) Applicant: OMRON HEALTHCARE Co., Ltd., Muko-shi, Kyoto (JP)

(72) Inventors: Hideyuki Yamashita, Kyoto (JP); Naoto Ohgami, Kyoto (JP); Toshiyuki Iwahori, Muko (JP); Hirotsugu Ueshima, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 0 days.

(21) Appl. No.: 14/173,143

(22) Filed: Feb. 5, 2014

(65) Prior Publication Data
US 2014/0207388 A1    Jul. 24, 2014

Related U.S. Application Data

(63) Continuation of application No. PCT/JP2012/066980, filed on Jul. 3, 2012.

(30) Foreign Application Priority Data

Aug. 5, 2011   (JP) .................................. 2011-172065

(51) Int. Cl.
*G01N 33/50* (2006.01)
*G01N 33/483* (2006.01)
(Continued)

(52) U.S. Cl.
CPC .......... *G01N 33/483* (2013.01); *G01N 33/493* (2013.01); *G01N 33/84* (2013.01)

(58) Field of Classification Search
CPC .. G01N 33/483; G01N 33/493; G01N 33/84; G01N 33/48; G01N 33/487; G01N 33/48707; G01N 33/50
See application file for complete search history.

(56) References Cited

U.S. PATENT DOCUMENTS

2009/0070046 A1*   3/2009   Kenjou et al. .................. 702/19

FOREIGN PATENT DOCUMENTS

| JP | A-10-213584 | 8/1998 |
| JP | A-2000-131316 | 5/2000 |

(Continued)

OTHER PUBLICATIONS

Kawasaki et al., "Studies on Estimation of 24-Hour Urinary Sodium Excretion from Predicted Creatinine Excretion and Fractional Urine Sodium/Creatinine Ratio," Journal of Health Science, 1986, vol. 8, pp. 57-63.

(Continued)

*Primary Examiner* — Manuel L Barbee
(74) *Attorney, Agent, or Firm* — Oliff PLC

(57) ABSTRACT

A urine component analysis device with a correlation storage section stores data indicating a correlation between a measured concentration of a specific component in human urine and measured concentration of the specific urine component in one day. A data input section inputs data indicating concentration of the specific component in one subject's urine. A concentration of the specific component in total urine of the subject in one day is determined by conversion using the correlation storage section based on the concentration of the specific component in the urine. A total urine amount acquirement section acquires total amount of urine excreted by the subject in one day based on conversion or database. An excretion amount of the specific component in total urine of the subject in one day is calculated by multiplying the concentration of the specific component in total urine in one day, by the acquired total urine amount.

14 Claims, 21 Drawing Sheets

(51) Int. Cl.
*G01N 33/84* (2006.01)
*G01N 33/493* (2006.01)

(56) References Cited

FOREIGN PATENT DOCUMENTS

| JP | A-2005-24267 | 1/2005 |
|---|---|---|
| JP | A-2006-29819 | 2/2006 |
| JP | A-2006-126184 | 5/2006 |
| JP | B2-3823039 | 9/2006 |
| JP | B2-4329123 | 9/2009 |
| WO | WO 2007/12345 A1 | 11/2007 |
| WO | WO 2007/123245 A1 | 11/2007 |

OTHER PUBLICATIONS

Kawasaki et al., "Studies on Estimation of 24-Hour Urinary Potassium Excretion from Predicted Cratinine Excretion and Fractional Urine Potassium/Creatinine Ratio," Journal of Health Science, 1987, vol. 9, pp. 133-136.

Tanaka et al., A Simple Method to Estimate Populational 24-H Urinary Sodium and Potassium Excretion Using a Casual Urine Specimen, Journal of Human Hypertension, 2002, vol. 16, pp. 97-103.

Office Action issued in Chinese Patent Application No. 201280038049.5 dated Sep. 12, 2014.

International Search Report issued in International Patent Application No. PCT/JP2012/066980 dated Sep. 18, 2012.

May 28, 2015 Office Action issued in Chinese Application No. 201280038049.5.

Nov. 10, 2015 Office Action issued in Chinese Patent Application No. 201280038049.5.

Mar. 31, 2016 Office Action issued in Chinese Patent Application No. 201280038049.5.

* cited by examiner

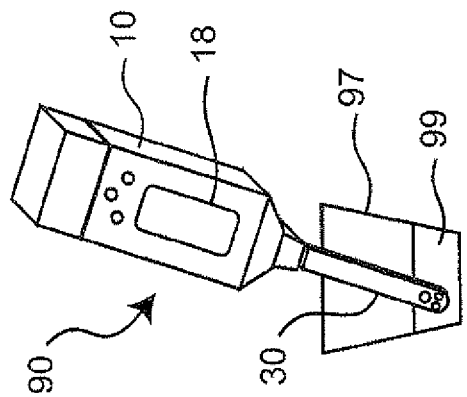
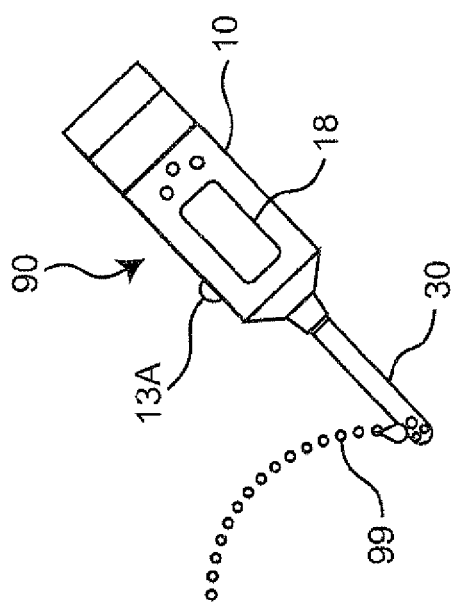

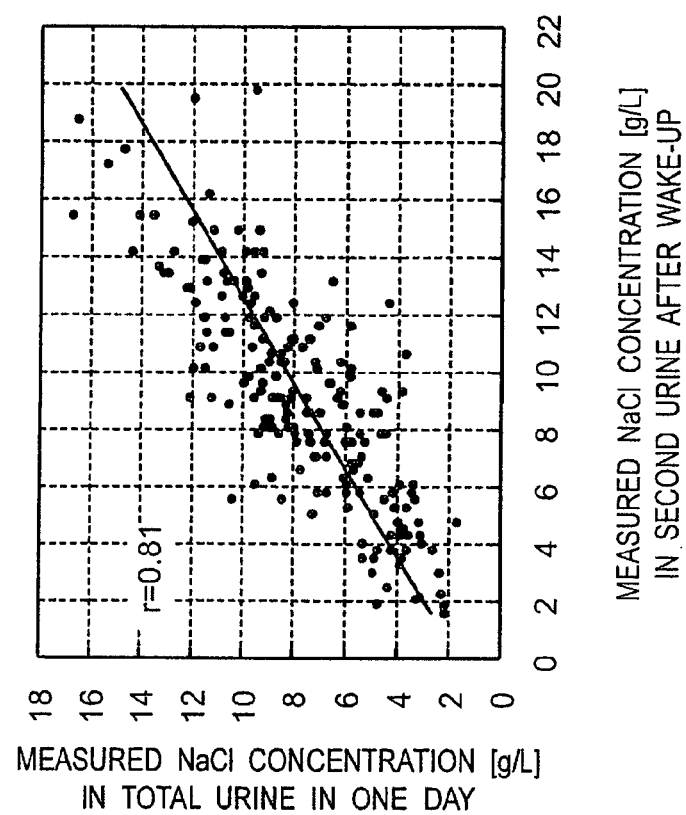
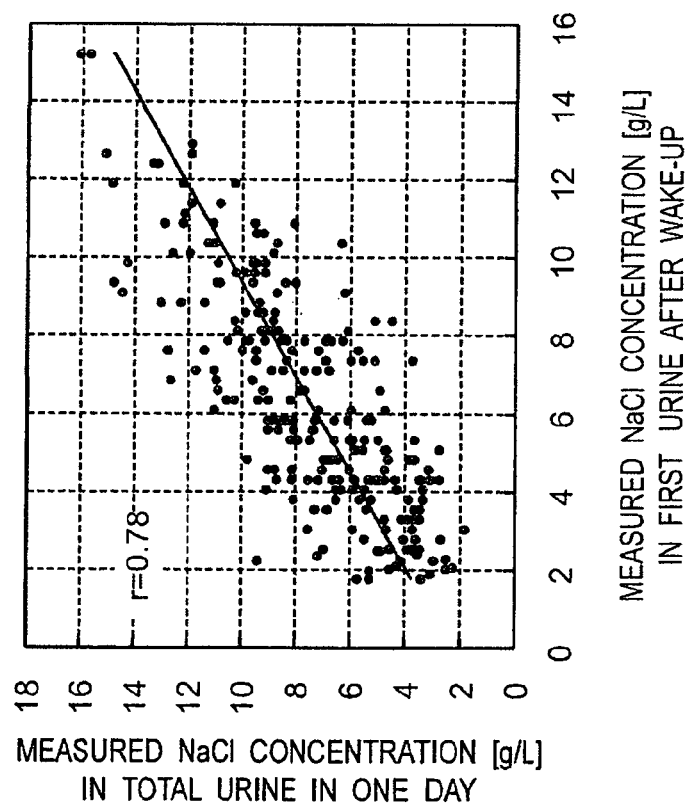

Fig.8
RESULT A OF EXAMINATION WITH MEASURED DAILY NaCl EXCRETION AMOUNT IN TOTAL URINE
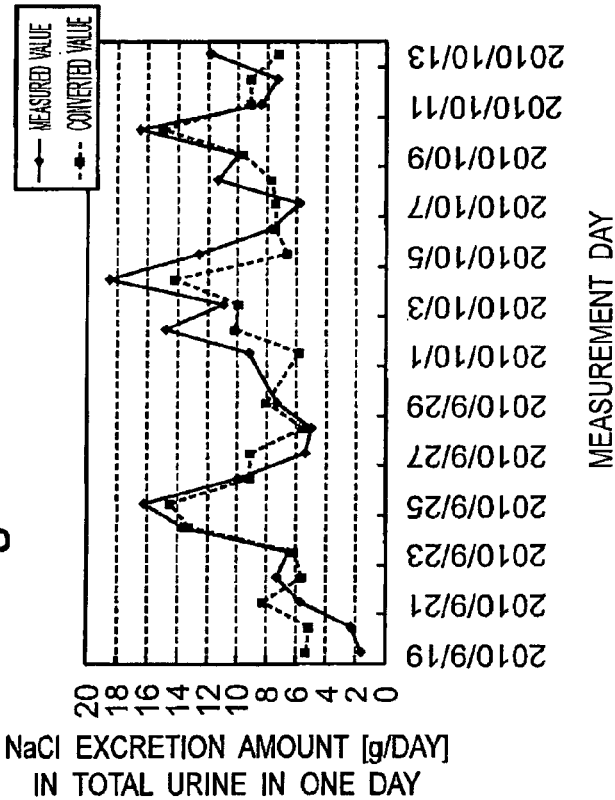
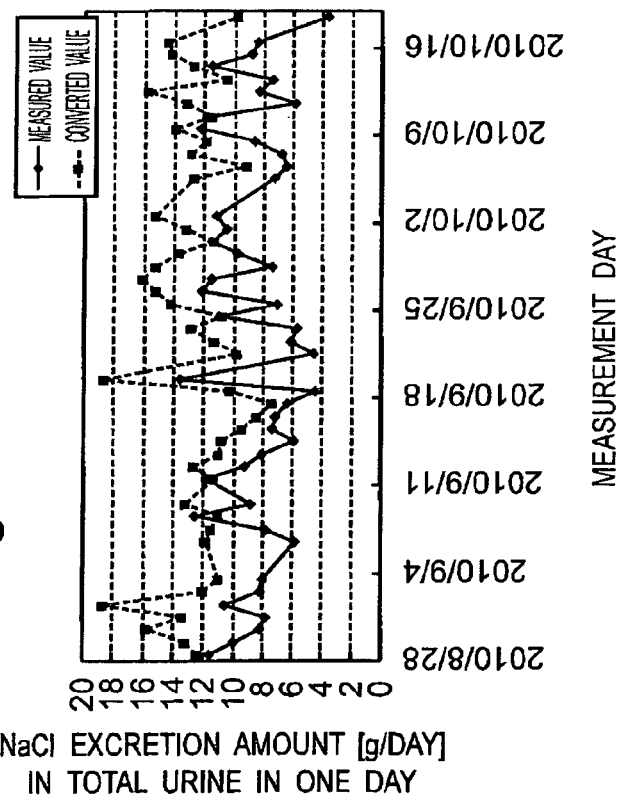

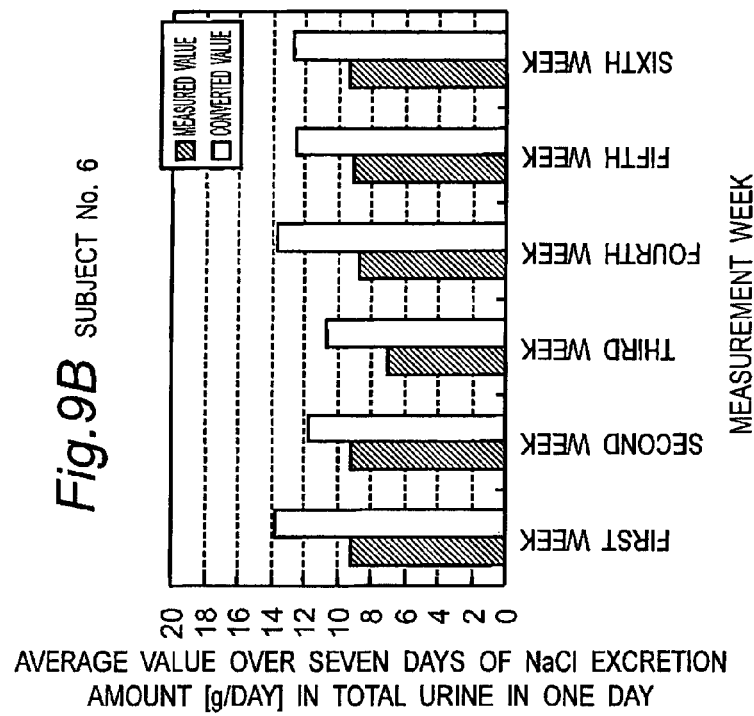
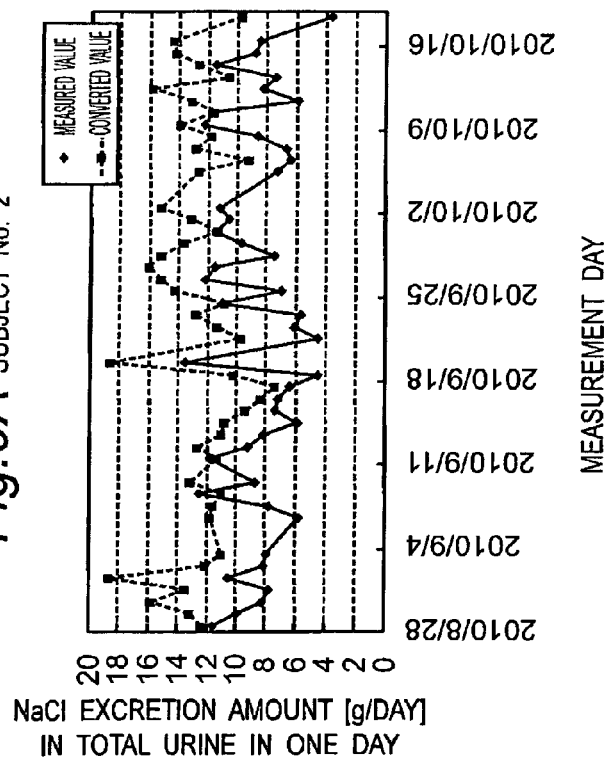
Fig. 9
RESULT B1 OF EXAMINATION WITH MEASURED DAILY AND WEEKLY NaCl EXCRETION AMOUNT IN TOTAL URINE

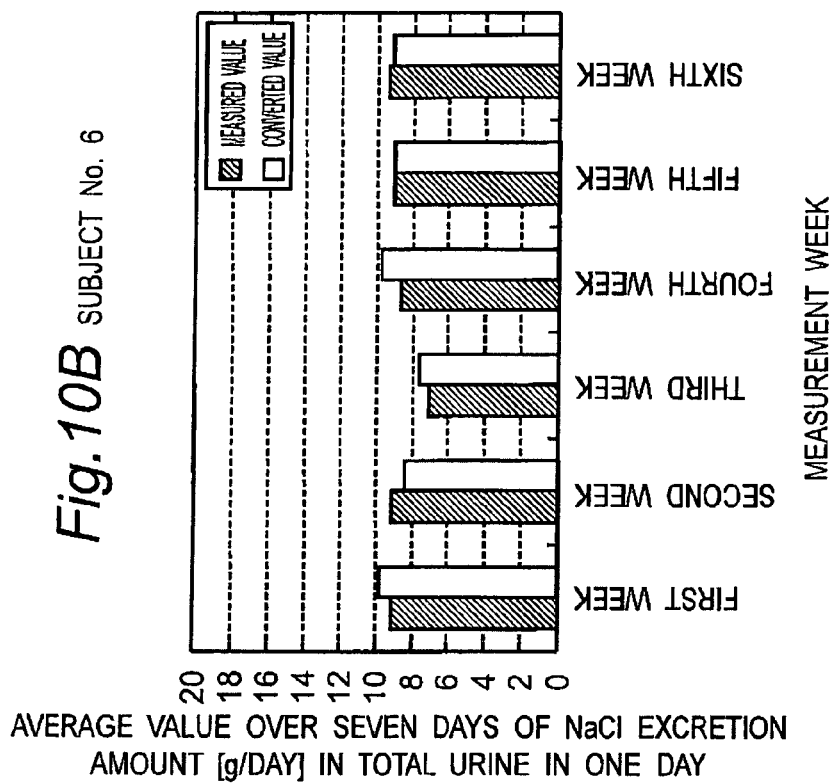
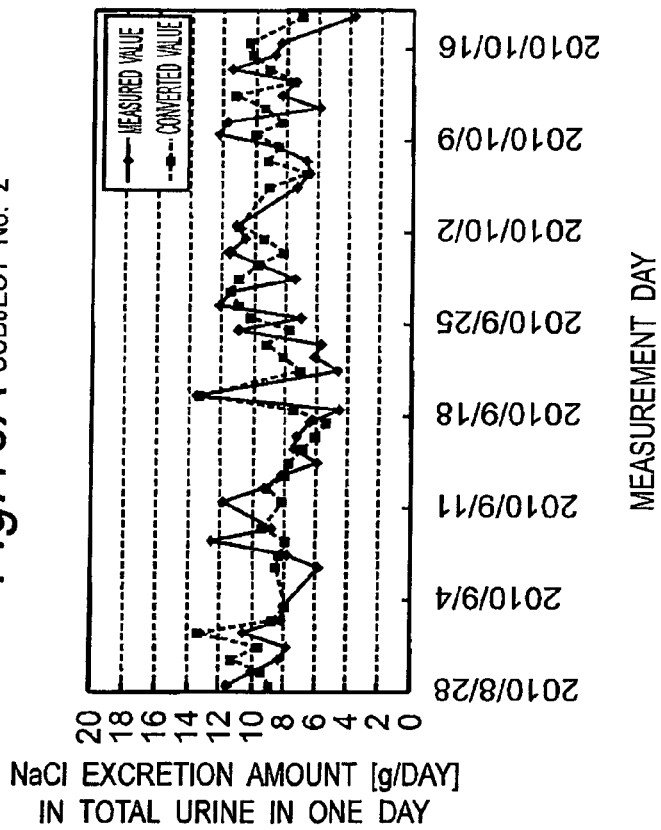
Fig.10 RESULT B2 OF EXAMINATION WITH MEASURED DAILY AND WEEKLY NaCl EXCRETION AMOUNT IN TOTAL URINE Fig. 11
RESULT B3 OF EXAMINATION WITH MEASURED DAILY AND WEEKLY NaCl EXCRETION AMOUNT IN TOTAL URINE
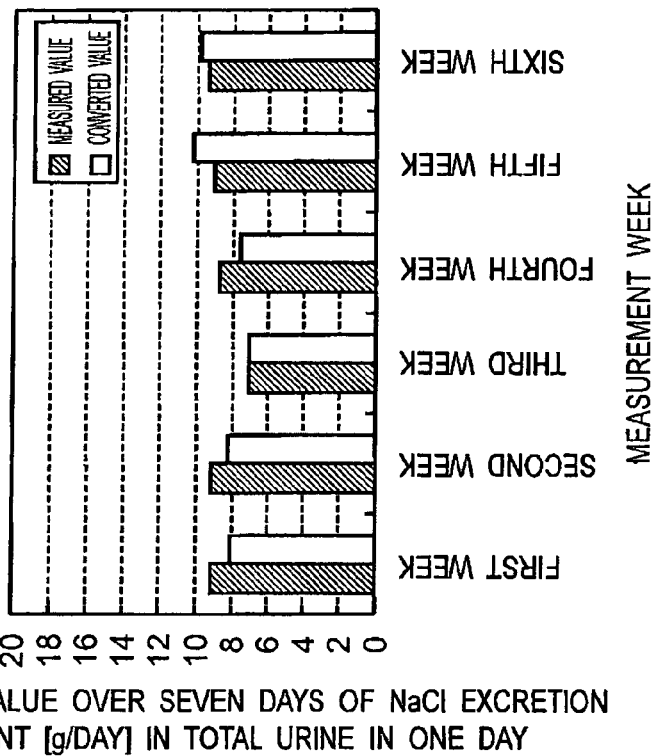
Fig. 11B SUBJECT No. 6
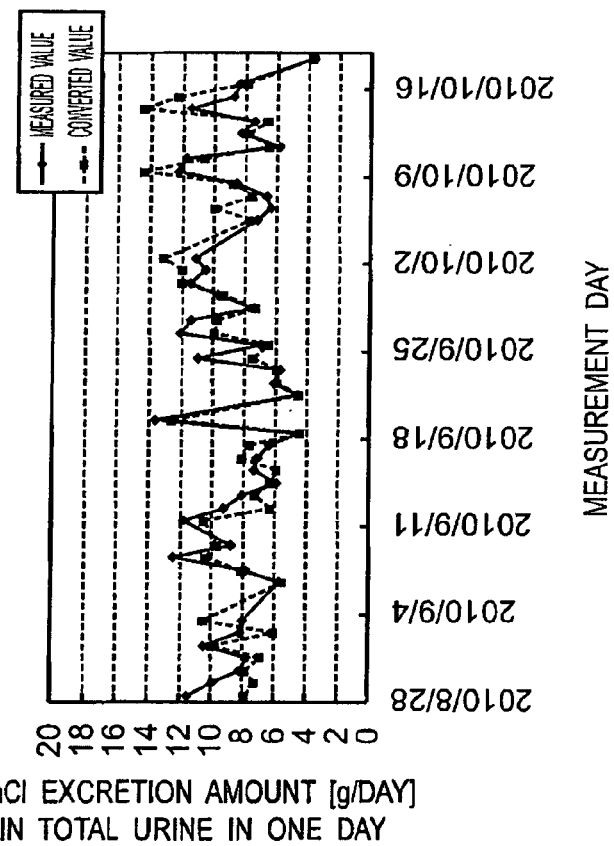
Fig. 11A SUBJECT No. 2

Fig. 13
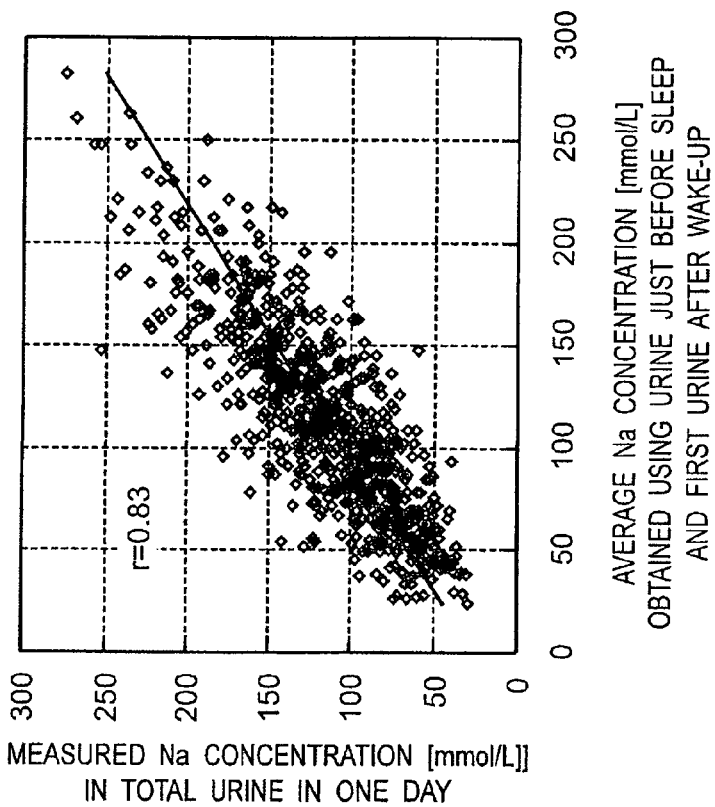
Fig. 13A
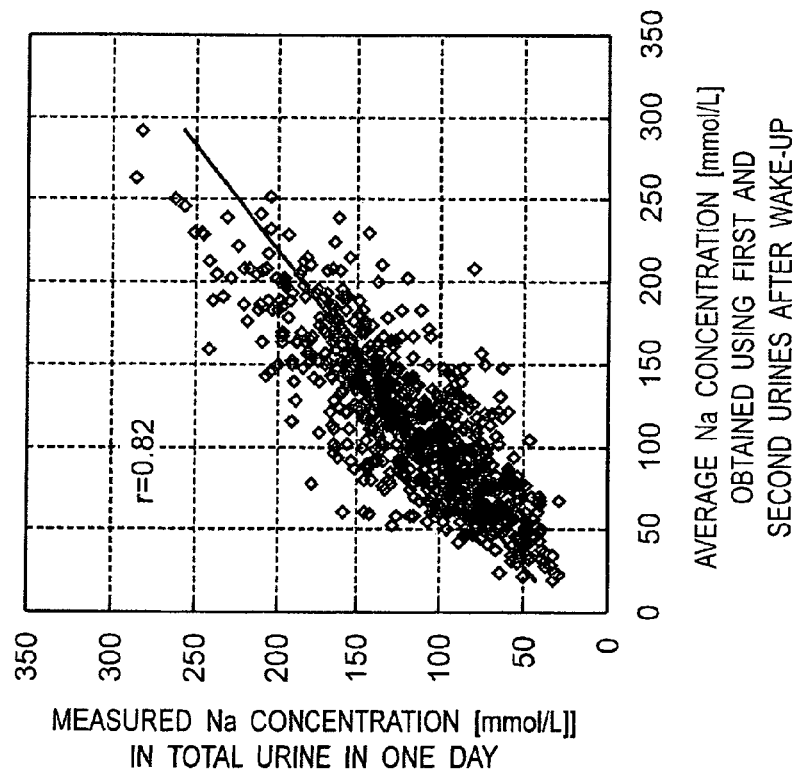
Fig. 13B

Fig.14
RESULT OF EXAMINATION WITH MEASURED Na EXCRETION AMOUNT IN TOTAL URINE IN ONE DAY
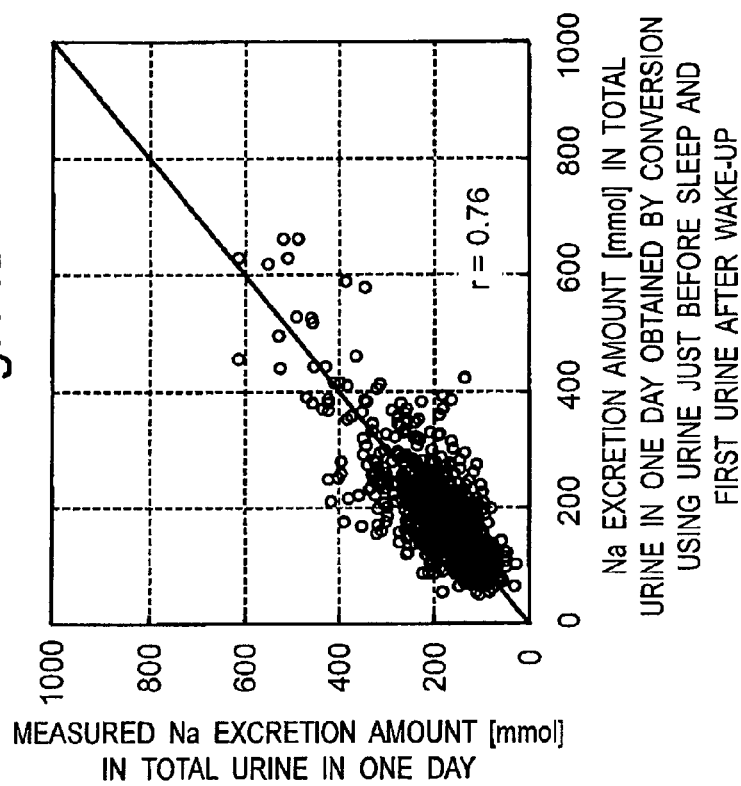
Fig.14A
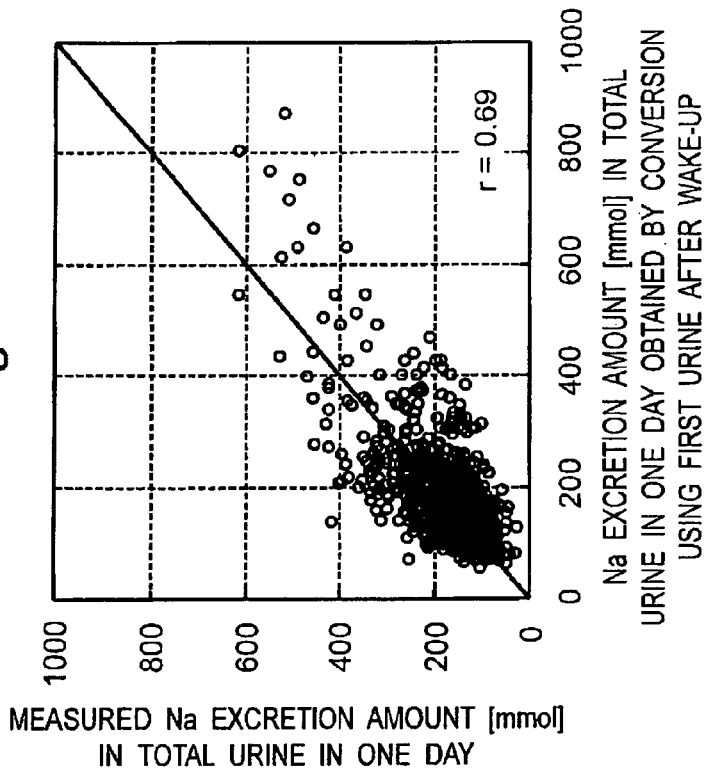
Fig.14B Fig. 15
RESULT A1 OF EXAMINATION WITH MEASURED Na EXCRETION AMOUNT IN TOTAL URINE OVER PLURAL DAYS
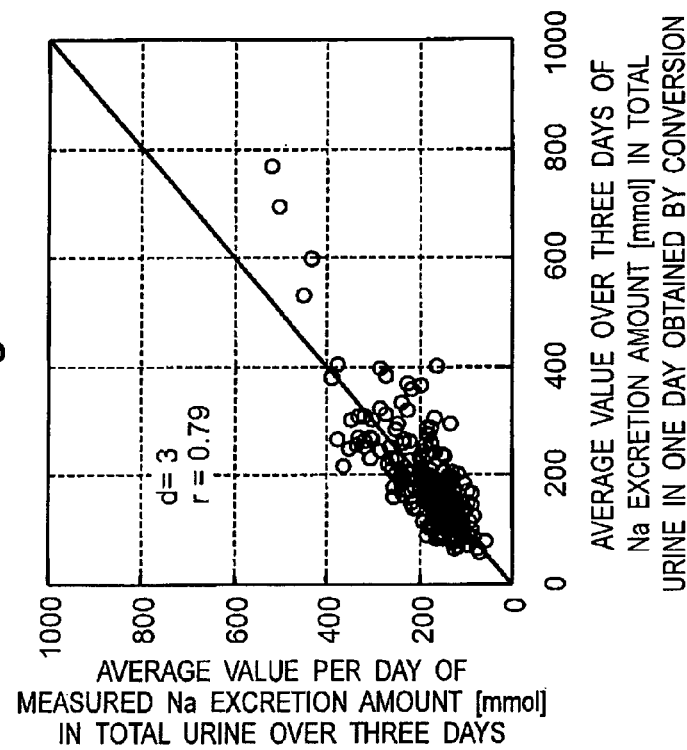
Fig.15A
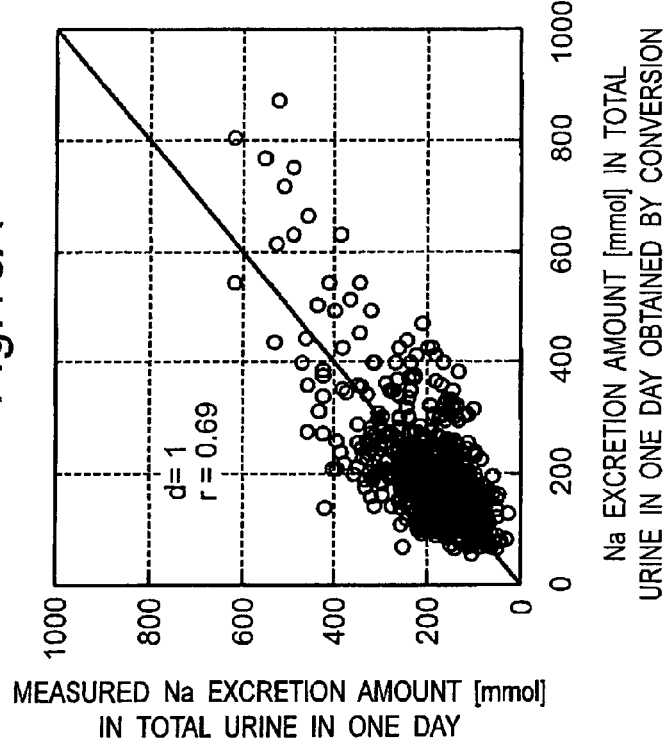
Fig.15B Fig. 16
RESULT A2 OF EXAMINATION WITH MEASURED Na EXCRETION AMOUNT IN TOTAL URINE OVER PLURAL DAYS
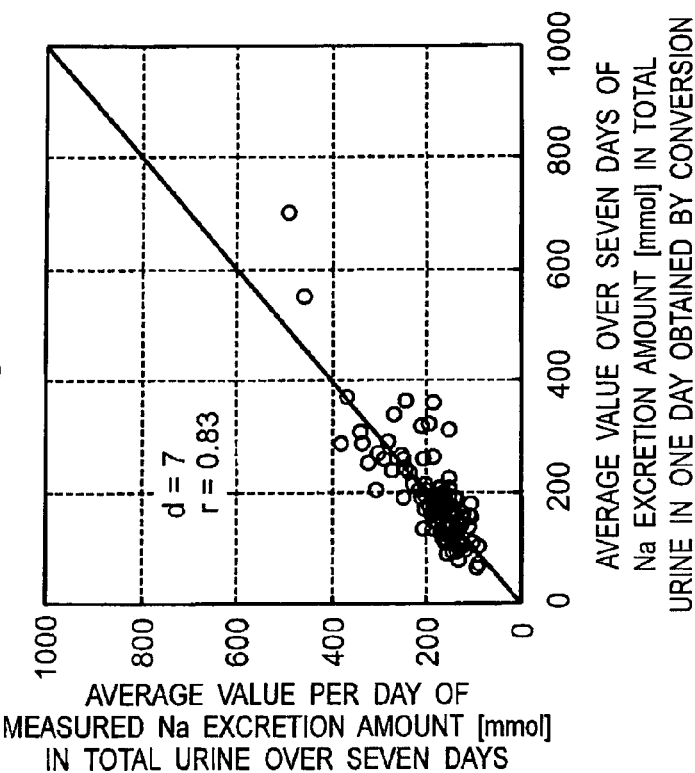
Fig. 16A
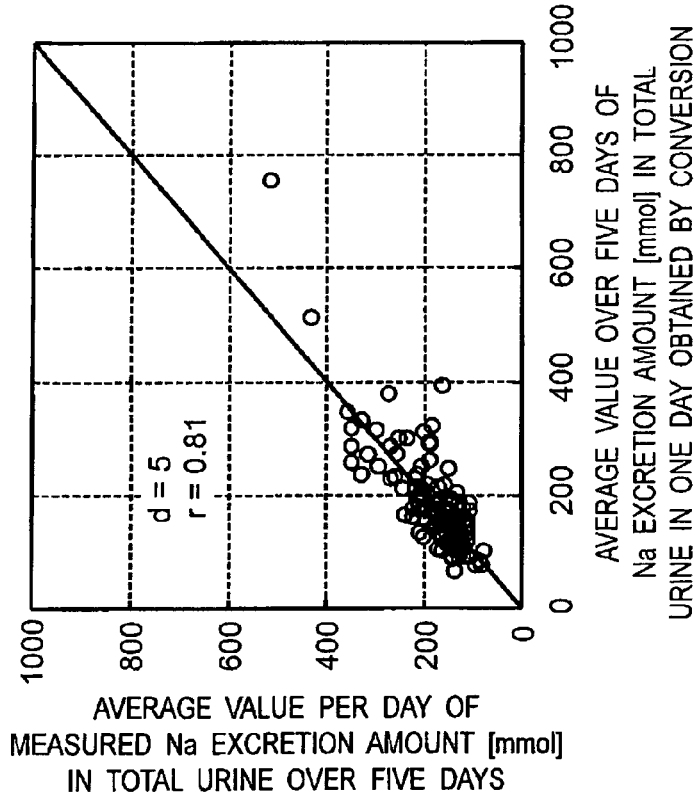
Fig. 16B

Fig.17
RESULT B1 OF EXAMINATION WITH MEASURED Na EXCRETION AMOUNT IN TOTAL URINE OVER PLURAL DAYS
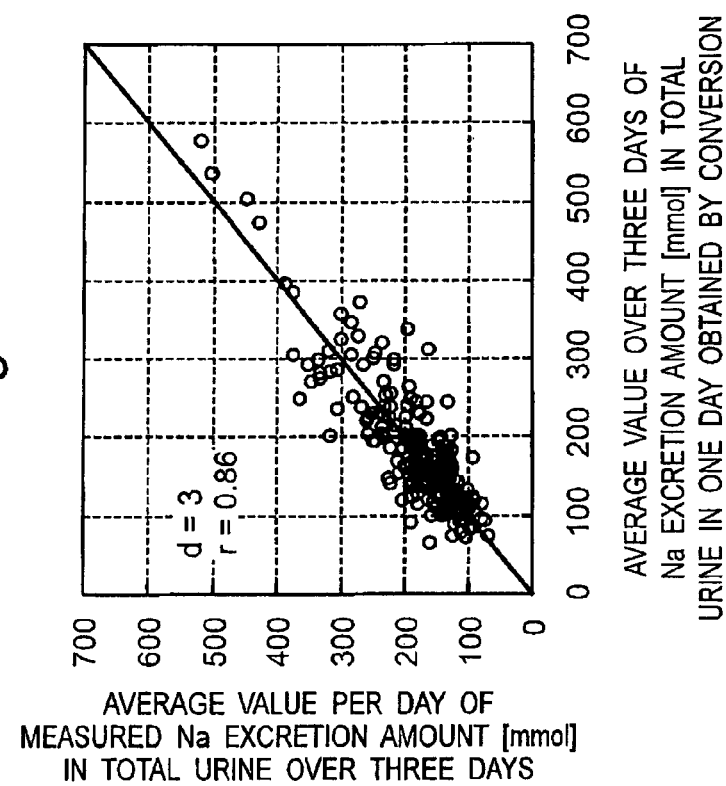
Fig.17B
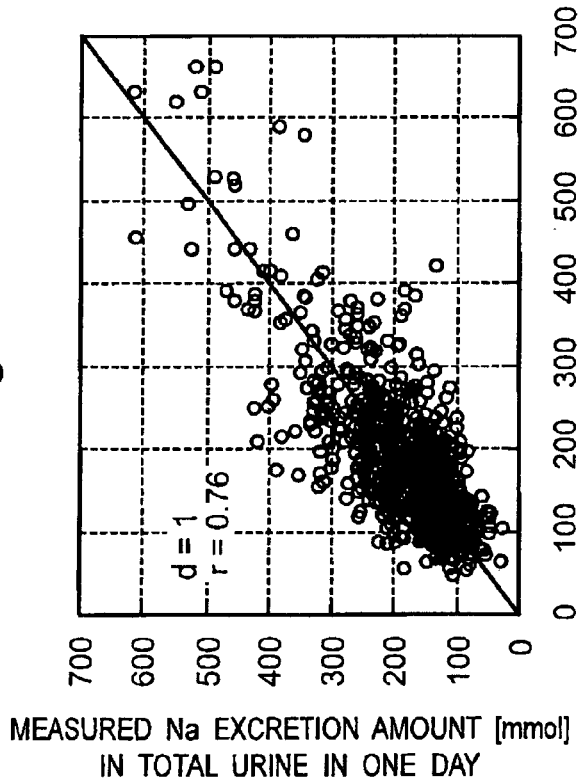
Fig.17A

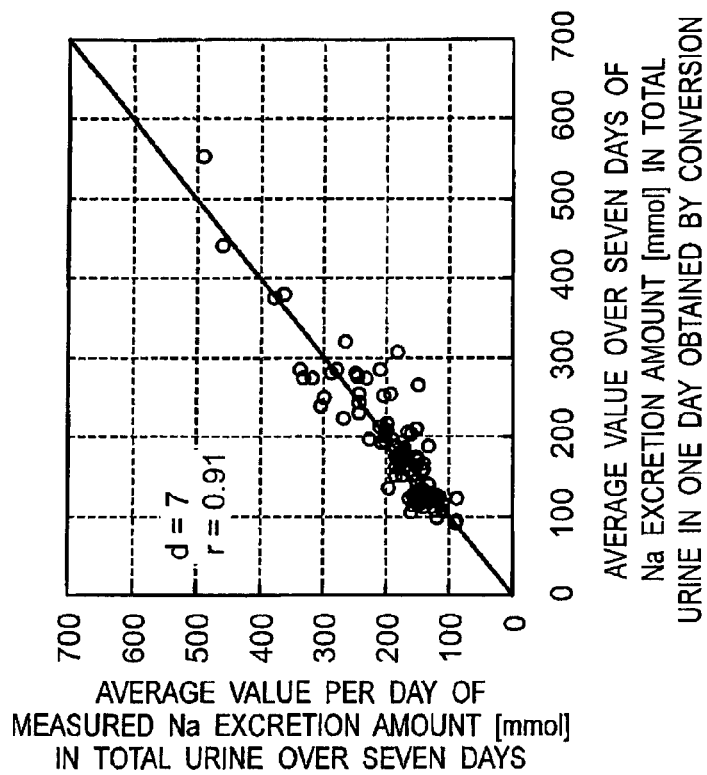
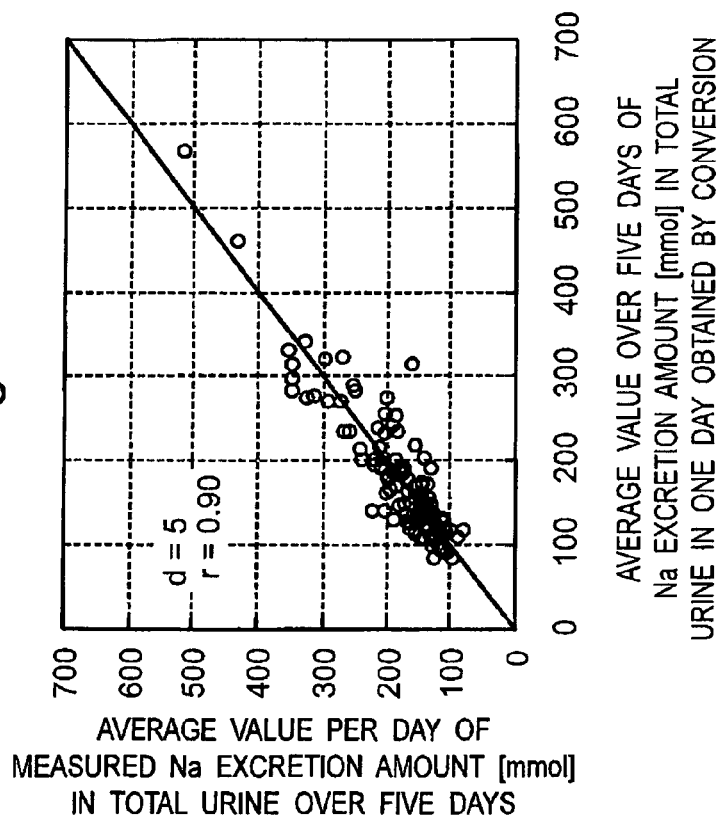

Fig.19

| SALINITY AMOUNT | ADVICE |
|---|---|
| 0-3g | IDEAL SALINITY INTAKE |
| 3-6g | SUCCESSFUL IN SALINITY REDUCTION |
| 6-7.5g | GOAL OF SALINITY REDUCTION WILL BE ACHIEVED WITH A LITTLE EFFORT |
| 7.5-9g | SALINITY INTAKE HIGH AND REDUCE SALINITY INTAKE |
| 9g OR MORE | SALINITY INTAKE SO HIGH. TAKE CARE OF YOUR DIETARY LIFE |

Fig.20

| SALINITY AMOUNT | BLOOD PRESSURE | BMI | ADVICE |
|---|---|---|---|
| 0.0-3.0g | LESS THAN 135/85 mmHg | LESS THAN 25 | IDEAL VALUE FOR BOTH SALINITY REDUCTION AND WEIGHT REDUCTION |
| | 135/85 mmHg OR MORE | 25 OR MORE | IDEAL VALUE FOR SALINITY REDUCTION. YOU NEED WEIGHT REDUCTION/EXERCISE AND MEDICATION" |
| | | LESS THAN 25 | GOAL ACHIEVED FOR SALINITY REDUCTION AND WEIGHT REDUCTION. YOU NEED CONTINUOUS MEDICATION |
| 3.0-6.0g | LESS THAN 135/85 mmHg | LESS THAN 25 | GOAL ACHIEVED FOR BOTH SALINITY REDUCTION AND WEIGHT REDUCTION |
| | 135/85 mmHg OR MORE | 25 OR MORE | GOAL ACHIEVED FOR SALINITY REDUCTION. YOU NEED WEIGHT REDUCTION/EXERCISE AND MEDICATION" |
| | | LESS THAN 25 | GOAL ACHIEVED FOR SALINITY REDUCTION AND WEIGHT REDUCTION. YOU NEED CONTINUOUS MEDICATION |
| 6-7.5g | LESS THAN 135/85 mmHg | LESS THAN 25 | GOAL WILL BE ACHIEVED WITH A LITTLE EFFORT FOR SALINITY REDUCTION. GOAL ACHIEVED FOR WEIGHT REDUCTION |
| | 135/85 mmHg OR MORE | 25 OR MORE | GOAL WILL BE ACHIEVED WITH A LITTLE EFFORT FOR SALINITY REDUCTION. YOU NEED WEIGHT REDUCTION/EXERCISE AND MEDICATION" |
| | | LESS THAN 25 | GOAL WILL BE ACHIEVED WITH A LITTLE EFFORT FOR SALINITY REDUCTION. GOAL ACHIEVED FOR WEIGHT REDUCTION/EXERCISE. YOU NEED CONTINUOUS MEDICATION |
| 7.5-9.0g | LESS THAN 135/85 mmHg | LESS THAN 25 | SALINITY AMOUNT HIGH AND TAKE CARE OF YOUR DIETARY LIFE. GOAL ACHIEVED FOR WEIGHT REDUCTION |
| | 135/85 mmHg OR MORE | 25 OR MORE | SALINITY AMOUNT HIGH AND TAKE CARE OF YOUR DIETARY LIFE. YOU NEED WEIGHT REDUCTION/EXERCISE AND MEDICATION" |
| | | LESS THAN 25 | SALINITY AMOUNT HIGH AND TAKE CARE OF YOUR DIETARY LIFE. GOAL ACHIEVED FOR WEIGHT REDUCTION/EXERCISE. YOU NEED CONTINUOUS MEDICATION |
| 9.0g OR MORE | LESS THAN 135/85 mmHg | LESS THAN 25 | SALINITY AMOUNT SO HIGH. TAKE ENOUGH CARE OF YOUR DIETARY LIFE. GOAL ACHIEVED FOR WEIGHT REDUCTION |
| | 135/85 mmHg OR MORE | 25 OR MORE | SALINITY AMOUNT SO HIGH. TAKE ENOUGH CARE OF YOUR DIETARY LIFE. YOU NEED WEIGHT REDUCTION/EXERCISE AND MEDICATION" |
| | | LESS THAN 25 | SALINITY AMOUNT SO HIGH. TAKE ENOUGH CARE OF YOUR DIETARY LIFE. GOAL ACHIEVED FOR WEIGHT REDUCTION/EXERCISE. YOU NEED CONTINUOUS MEDICATION |

URINE COMPONENT ANALYSIS DEVICE AND URINE COMPONENT ANALYSIS METHOD

CROSS-REFERENCE TO RELATED APPLICATIONS

This is a continuation application of International Application No PCT/JP2012/066980, with an International filing date of Jul. 3, 2012, which claims priority of Japanese Patent Application No. 2011-172065 filed on Aug. 5, 2011, the entire content of which is hereby incorporated by reference.

TECHNICAL FIELD

The present invention relates to a urine component analysis device and a urine component analysis method, and more particularly to a urine component analysis device and a urine component analysis method for determining an excretion amount of specific components in urine of a subject.

BACKGROUND ART

As a technique for analyzing a urine component, a method has been heretofore known in which a urine transport container including an inner tube and an outer tube is provided, and based on a weight or volume of urine collected in the inner tube, a total amount of urine collected first is determined and excretion amounts of components in the collected urine are measured as disclosed in, for example, Patent Document 1 (Japanese Patent Publication No. 3823039).

A method is known in which an amount of first urine after wake-up, which is excreted by a human, and a concentration of a specific component are measured to determine an excretion amount of the specific component in the first urine after wake-up and an elapsed time from urine discharge before sleep to first urine discharge after wake-up is acquired, the excretion amount of the specific component is converted into a defined time equivalent based on a ratio of the elapsed time to a preset defined time, and an excretion amount of the specific component excreted by the human in one day is calculated based on the converted defined time equivalent as disclosed in Patent Document 2 (Japanese Patent Publication No. 4329123).

A method is known in which a salinity concentration in the urine excreted by a human is measured, the measured salinity concentration in the urine is multiplied by a total amount of urine excreted by the human in one day to determine a total amount of salinity excreted by the human in one day, and a salinity intake amount of the human in one day is calculated based on the determined total amount of salinity as disclosed in Patent Document 3 (Japanese Patent Laid-open Publication No. 10-213584). It is described that as the total amount of urine excreted by the human in one day, for example, a known value such as an average urine amount per day of Japanese may be used, or a value of a total amount of urine excreted in one day, which is measured by a subject, may be used.

SUMMARY OF THE INVENTION

As a dietary therapy for hypertensive patients, salinity reduction and intake of potassium are generally recommended. According to a reliable document ("Details of Diet Survey Nutritional Epidemiology" written by Walter Willette, translated by Heizo Tanaka; 2nd edition; DAIICHI SYUPPAN CO., LTD; May 2003), sodium and potassium ingested by a human through diet are excreted into urine in ratios of 86% and 77%, respectively. Therefore, results of examining a sodium excretion amount (Na excretion amount) and a potassium excretion amount (K excretion amount), particularly a ratio between a sodium excretion amount and a potassium excretion amount (Na/K ratio), in every-day urine can be reflected in dietary therapies for hypertensive patients.

However, the method in Patent Document 1 (Japanese Patent Publication No. 3823039) has a problem that when measurement is performed every day over a long period of time, a subject is required to collect a part of urine every time the subject discharges urine, thus causing a nuisance to the subject. For example, it is quite a nuisance and difficult to practice on a daily basis that a subject goes out with a container and collects urine at a place of visit.

Also, the method in Patent Document 2 (Japanese Patent Publication No. 4329123) has a problem that although only the first urine after wake-up is required, it is necessary to collect all the urine and measure an amount of urine, thus causing a nuisance to the subject. That is, when considering a case where the amount of one urine of a subject is relatively large, the subject is required to provide a relatively large-volume container of about 1 liter. Further, when the subject repeatedly uses the container, it takes time and labor to wash the relatively large-volume container. When a function to measure an amount of one urine is added to a toilet bowl, installation of a very large-scaled device is required.

On the other hand, in the method in Patent Document 3 (Japanese Patent Laid-open Publication No 10-213584), time and labor for urine amount measurement is saved when for example, a known value such as an average urine amount per day of Japanese as described above is used as a total amount of urine excreted by a human in one day. However, the salinity concentration in the urine excreted by a human varies each time urine is discharged. Therefore, the method in this document has a problem of poor calculation accuracy.

Thus, an object of the present invention is to provide a urine component analysis device and a urine component analysis method which are capable of easily and conveniently and accurately determining an excretion amount of a specific component in total urine of a subject in one day.

For achieving the object described above, a urine component analysis device of the present invention comprises:

a correlation storage section which stores data indicating a correlation between a concentration of a specific component in one urine excreted by a human and a concentration of the specific component in total urine in one day when all the urine excreted by the human in the one day is gathered into one volume;

a total urine amount acquirement section which acquires a total amount of urine excreted by a subject in one day based on conversion or a database;

a data input section which inputs data indicating a concentration of the specific component in one urine excreted by the subject;

a first calculation section which determines a concentration of the specific component in total urine in one day when all the urine excreted by the subject in the one day is gathered into one volume, by performing conversion using the correlation stored in the correlation storage section, based on the concentration of the specific component in the one urine of the subject obtained via the data input section; and a second calculation section which calculates an excretion amount of the specific component in the total urine of the subject in the one day by multiplying the concentration of the specific component in the total urine in the one day, which is determined by the first calculation section, by the total urine amount in the one day acquired by the total urine amount acquirement section.

In this specification, the "human" may be identical to the "subject". The "human" may include a plurality of persons, and may include the "subject" in this case.

In another aspect, the urine component analysis method of the present invention comprises:

storing in a predetermined storage section data indicating a correlation between a concentration of a specific component in one urine excreted by a human and a concentration of the specific component in total urine in one day when all the urine excreted by the human in the one day is gathered into one volume;

acquiring a total amount of urine excreted by a subject in one day based on conversion or a database, and inputting data indicating a concentration of the specific component in one urine excreted by the subject;

determining a concentration of the specific component in total urine in one day when all the urine excreted by the subject in the one day is gathered into one volume, by performing conversion using the correlation stored in the storage section, based on the input concentration of the specific component in the one urine of the subject; and calculating an excretion amount of the specific component in the total urine of the subject in the one day by multiplying the determined concentration of the specific component in the total urine in the one day by the total urine amount in the one day acquired based on conversion or a database.

According to a urine component analysis device and a urine component analysis method of the present invention, an excretion amount of a specific component in total urine of a subject in one day can be easily and conveniently and accurately determined.

BRIEF DESCRIPTION OF THE DRAWINGS

The present invention will become more fully understood from the detailed description given hereinbelow and the accompanying drawings which are given by way of illustration only and thus are not limitative of the present invention, and wherein:

FIGS. 2A and 2B are views each showing an aspect in which the urine component analysis device is used.

FIGS. 5A and 5B of FIG. 5 are views each showing a correlation between a measured NaCl concentration in one urine and a measured NaCl concentration in total urine in one day.

FIGS. 8A and 8B of FIG. 8 are views showing, for subjects No. 2 and No. 6 respectively, a result of examining a daily NaCl excretion amount in total urine, which is obtained by conversion using one urine, by using a measured daily NaCl excretion amount in total urine.

FIG. 9A of FIG. 9 is a view showing, for subject No. 2, a result of examining a daily NaCl excretion amount in total urine, which is obtained by conversion using one urine, by using a measured daily NaCl excretion amount in total urine, under the condition that total urine amount in one day is acquired by referring to a database. FIG. 9B of FIG. 9 is a view showing average values obtained by averaging, respectively, the converted value and the measured value in FIG. 9A for each week.

FIG. 10A of FIG. 10 is a view showing, for subject No. 2, a result of examining a daily NaCl excretion amount in total urine, which is obtained by conversion using one urine, by using a measured daily NaCl excretion amount in total urine, under the condition that total urine amount in one day is acquired by converting total urine amount during a sampling period by a number of days. FIG. 10B of FIG. 10 is a view showing average values obtained by averaging, respectively, the converted value and the measured value in FIG. 10A for each week.

FIG. 11A of FIG. 11 is a view showing, for subject No. 2, a result of examining a daily NaCl excretion amount in total urine, which is obtained by conversion using one urine, by using a measured daily NaCl excretion amount in total urine, under the condition that total urine amount in one day is acquired by performing measurement. FIG. 11B of FIG. 11 is a view showing average values obtained by averaging, respectively, the converted value and the measured value in FIG. 11A for each week.

FIG. 13A of FIG. 13 is, a view showing a correlation between an average Na concentration obtained using two urines (first and second urines after wake-up) and a measured Na concentration in total urine in one day. FIG. 13B of FIG. 13 is a view showing a correlation between an average Na concentration obtained using two urines (urine just before sleep and first urine after wake-up) and a measured Na concentration in total urine in one day.

FIGS. 14A and 14B of FIG. 14 are views showing results of examining a Na excretion amount in total urine in one day, which is obtained by conversion using one urine and two urines, respectively, by using a measured Na excretion amount in total urine per day.

FIG. 15A of FIG. 15 is a view showing a result of examining a Na excretion amount total urine in one day, which is obtained by conversion using one urine, by using a measured Na excretion amount in total urine in one day. FIG. 15B of FIG. 15 is a view showing a result of examining an average value over three days of the Na excretion amount in total urine in one day, which is obtained by conversion using one urine, by using an average value per day of the measured Na excretion amount in total urine over three days.

FIG. 16A of FIG. 16 is a view showing a result of examining an average value over five days of the Na excretion amount in total urine in one day, which is obtained by conversion using one urine, by using an average value per day of the measured Na excretion amount in total urine over five days. FIG. 16B of FIG. 16 is a view showing a result of examining an average value over seven days of the Na excretion amount in total urine in one day, which is obtained by conversion using one urine, by using an average value per day of the measured Na excretion amount in total urine over seven days.

FIG. 17A of FIG. 17 is a view showing a result of examining a Na excretion amount in total urine in one day, which is obtained by conversion using two urines, by using a measured Na excretion amount in total urine in one day. FIG. 17B of FIG. 17 is a view showing a result of examining an average value over three days of the Na excretion amount in total urine in one day, which is obtained by conversion using two urines, by using an average value per day of the measured Na excretion amount in total urine over three days.

FIG. 18A of FIG. 18 is a view showing a result of examining an average value over five days of the Na excretion amount in total urine in one day, which is obtained by conversion using two urines, by using an average value per day of the measured Na excretion amount in total urine over five days. FIG. 18B of FIG. 18 is a view showing a result of examining an average value over seven days of the Na excretion amount in total urine in one day, which is obtained by conversion using two urines, by using an average value per day of the measured Na excretion amount in total urine over seven days.

FIG. 19 is a view showing one example of the contents of an advice table.

FIG. 20 is a view showing another example of the contents of an advice table.

DESCRIPTION OF EMBODIMENTS

Hereinafter, the present invention will be described in detail by way of illustrated embodiments.

First Embodiment

Figure 1:
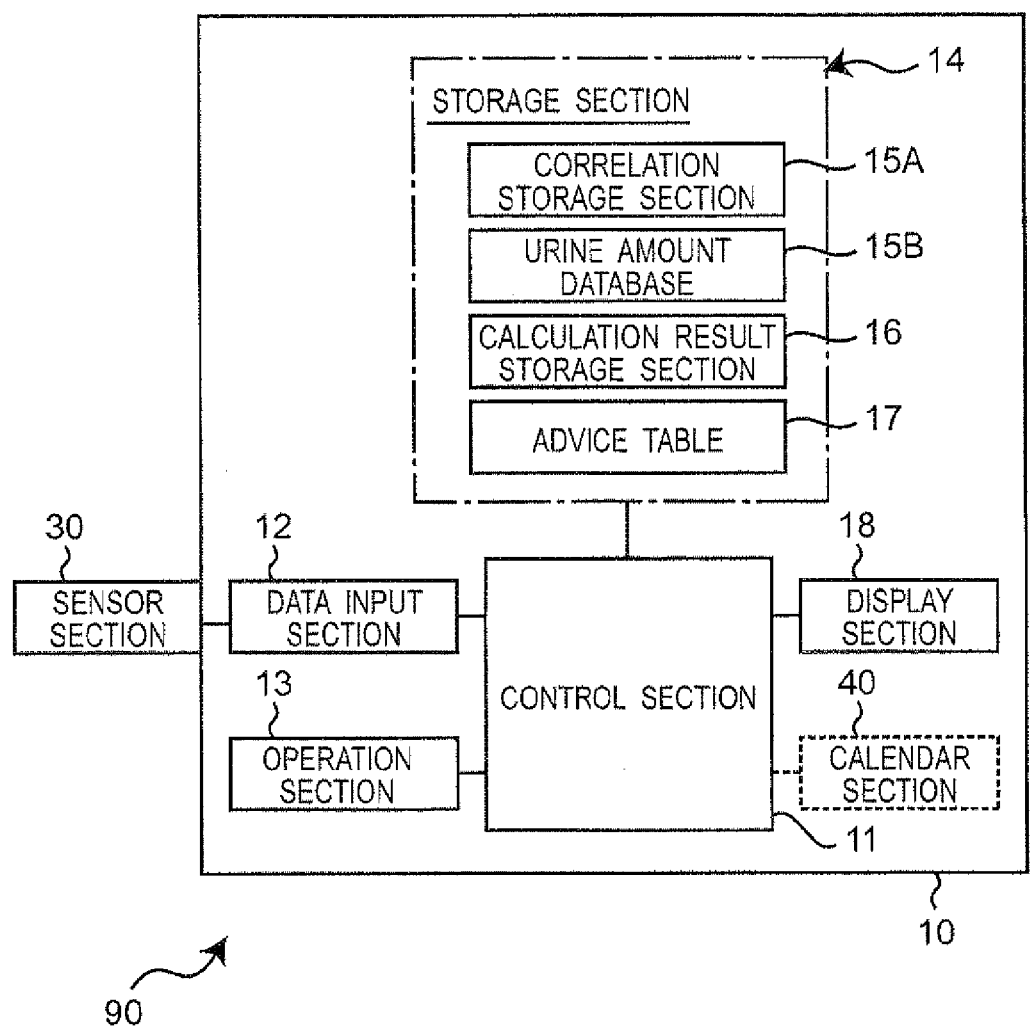
FIG. 1 is a view showing a block configuration of a urine component analysis device of one embodiment of the present invention.

FIG. 1 shows a block configuration of a urine component analysis device (denoted by symbol 90 as a whole) of one embodiment of the present invention.

The urine component analysis device 90 includes a housing 10, a control section 11 mounted and stored in the housing 10, a data input section 12, an operation section 13, a storage section 14 and a display section 18 as a notification section. Further, the urine component analysis device 90 includes a sensor section 30 attached to the housing 10 so as to be projected to outside from the housing 10.

In this example, the housing 10 has a narrow and long prism-like external shape so that the housing is held by the user's hand as shown in FIG. 2A. The sensor section 30 is attached at one end of the housing 10 and has a narrow and long rod-like external shape. As a result, the urine component analysis device 90 is formed as a hand-held type urine component analysis device that is used by a user with the housing 10 held in the hand.

The sensor section 30 is one publicly known, and it comes into contact with urine 99 excreted by the subject to acquire data about a concentration of a specific component in the urine. In this example, the specific component is salt (NaCl. Referred to as "salinity" as appropriate). In this example, the sensor section 30 may acquire data indicating a NaCl concentration (or Na concentration) in one urine 99.

For example, when the hand-held type urine component analysis device 90 is used, urine is spritzed on the sensor section 30 as shown in FIG. 2A with the housing 10 held in the hand when the subject as a user discharges urine. In this way, the sensor section 30 can come into contact with urine excreted by the subject to acquire data about a NaCl concentration.

Alternatively, when the subject as a user discharges urine, the subject may collect a part of one urine 99 in a disposable paper cup 97, and immerse the sensor section 30 in the urine 99 in the paper cup 97 with the housing 10 held in the hand as shown in FIG. 2B.

Alternatively, when the subject as a user discharges urine, the subject may infiltrate a part of one urine into a sheet of toilet paper (not illustrated), and bring the sensor section 30 into contact with the urine infiltrated in the sheet of toilet paper with the housing 10 held in the hand.

In any case, according to the hand-held type urine component analysis device, a later-described calculation result is obtained by simple operations.

The control section 11 shown in FIG. 11 includes a CPU (central processing unit) operated by software, and acts as a first calculation section and a second calculation section etc. to execute various kinds of processing.

The data input section 12 inputs, in real time in this example, data about a concentration of a specific component in the urine acquired by the sensor section 30.

The operation section 13 includes a scroll button 13A shown in FIG. 2A, and acts to input various kinds of information from the user. Examples of information to be input include urine specification information indicating whether urine to be measured is the first urine after wake-up or the second urine after wake-up or the urine just before sleep, and information indicating a sex, an age, a blood pressure and a EMI (body mass index) of the subject. When urine specification information is input, the operation section 13 acts as a urine specification section.

The storage section 14 includes an EEPROM (an electrically rewritable nonvolatile memory) in this example, and includes a correlation storage section 15A, a urine amount data base 15B, a calculation result storage section 15 and an advice table 17.

As shown in, for example, FIGS. 5A and 5B, the correlation storage section 15A stores data indicating a correlation between a measured NaCl concentration in one urine and a measured NaCl concentration in total urine in one day (dots in the figure each represent measured data). Specifically, FIG. 5A shows a case where a relationship between a measured NaCl concentration in the first urine after wake-up (abscissa x, unit: [g/L]) and a measured NaCl concentration in total urine in one day (ordinate y, unit: [g/L]) is approximated by a straight line (shown by a solid line in FIG. 5A), and an expression of the straight line is stored as data indicating a correlation. In this case, it is shown that there is a high correlation with the correlation coefficient being r=0.78. FIG. 5B shows a case where a relationship between a measured NaCl concentration in the second urine after wake-up (abscissa x, unit: [g/L]) and a measured NaCl concentration in total urine in one day (ordinate y, unit: [g/L]) is similarly approximated by a straight line (shown by a solid line in FIG. 5B), and an expression of the straight line is stored as data indicating a correlation. In this case, it is shown that the correlation coefficient is r=0.81.

A case where an expression approximated by a straight line is stored as data indicating a correlation has been described as an example, but the present invention is not limited to this example. The correlation storage section 15A may store other functions, conversion databases and the like.

The measured NaCl concentration (or Na concentration) and later-described NaCl excretion amount (or Na excretion amount) in total urine of a subject are measured after all the urine excreted by the subject is gathered into one volume (stored-urine method; the same hereinafter).

Figure 6:
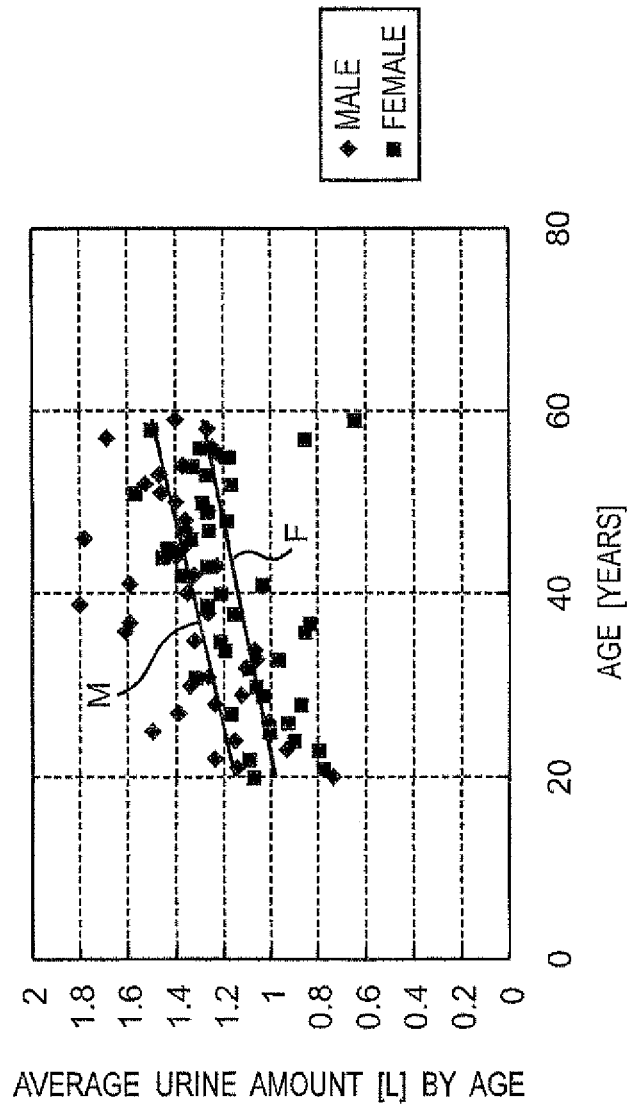
FIG. 6 is a view illustrating a database storing a total urine amount per day of a human.

The urine amount database 153 stores data indicating a total urine amount per day of a human in accordance with sex and age as shown in, for example, FIG. 6. In FIG. 6, the abscissa represents age (years) and the ordinate represents a total urine amount per day (average urine amount by age) (L), where dots in the figure each represent measured data. For the male, a case is shown where a relationship between age and a total urine amount per day is approximated by a straight line (shown by a solid line M in FIG. 6), and an expression of the straight line is stored as data indicating a correlation. In this case, the dispersion is $R^2=0.2243$. For the female, a case is shown where a relationship between age and a total urine amount per day is approximated by a straight line (shown by a solid line F in FIG. 6), and an expression of the straight line is stored as data indicating a correlation. In this case, the dispersion is $R^2=0.1882$. It is apparent that when conditions of sex and age are specified (input), a total urine amount per day of a human can be acquired by referring to the urine amount database 15B. Data in FIG. 6 is data measured by the present inventor.

The advice table 17 stores a salinity amount (NaCl amount) in correspondence with advices appropriate to the salinity amount for the subject as shown in, for example, FIG. 19. For example, the advice of "Ideal salinity intake" corresponds to a salinity amount falling within a range of 0 to 3 g. The advice of "Successful in salinity reduction" corresponds to a salinity amount falling within a range of 3 to 6 g. The advice of "Goal will be achieved with a little effort" corresponds to a salinity amount falling within a range of 6 to 7.5 g. The advice of "Salinity intake high and reduce salinity intake" corresponds to a salinity amount falling within a range of 7.5 to 9 g. The advice of "Salinity intake so high and take care of your dietary life" corresponds to a salinity amount of 9 g or more. The value range segmentation of the salinity amount in the advice table 17 is one example, and it is also possible to make a setting with the value range segmentation changed.

The calculation result storage section 16 shown in FIG. 1 sequentially stores calculation results (later-described NaCl concentration or Na concentration) in total urine of a subject in one day) from the control section 11 in correspondence with measurement dates and times, respectively. For example, the user can easily know a tendency of daily change in NaCl concentration (or Na concentration) in total urine of the subject in one day by reading the contents of the calculation result storage section.

The display section 18 includes an LCD (liquid crystal display device) (see FIG. 2A) in this example, and displays various kinds of information such as a calculation result from the control section 11.

Figure 3:
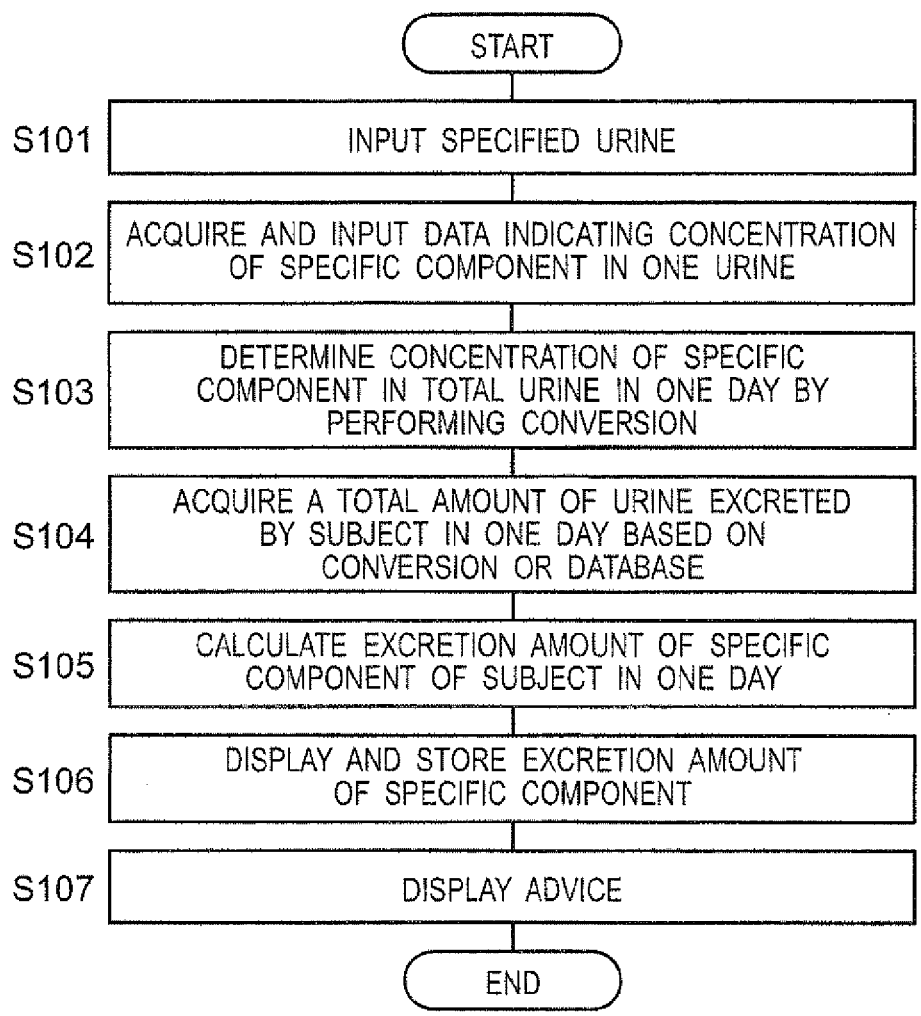
FIG. 3 is a view showing one example of an operational flow of the urine component analysis device.

The urine component analysis device 90 is operated under control by the control section 11 generally in accordance with a flow shown in, for example, FIG. 3.

i) First, for example when a user turns on a power switch (not illustrated), a urine specification mode is started as shown in Step S101 in FIG. 3.

In this example, the control section 11 acts as a urine specification section to display options of "first urine after wake-up", "second urine after wake-up" and "urine just before sleep" etc. on the display section 18 in the urine specification mode. When the user rotates a scroll button 13A as these options are displayed, options of "first urine after wake-up", "second urine after wake-up" and "urine just before sleep" etc. are sequentially highlighted as a selection candidate. For example, when the user depresses the scroll button 13A while "first urine after wake-up" is highlighted, "first urine after wake-up" is input as the urine to be measured. In a manner described above, the user inputs, via the operation section 13, urine specification information indicating whether urine to be measured is the first urine after wake-up or the second urine after wake-up or the urine just before sleep. When input of urine specification information is completed, a urine measurement mode is started.

If urine to be measured is always limited to, for example, "first urine after wake-up", the urine specification mode (Step S101) can be skipped.

ii) Next, in the urine measurement mode, the user spritzes the urine 99 on the sensor section 30 as shown in, for example, FIG. 2A, and depresses the scroll button 13A. Then, as shown in Step S102 in FIG. 3, the sensor section 30 acquires data indicating a NaCl concentration in one urine 99, and the data input section 12 inputs in real time the data indicating a NaCl concentration in this example.

When this data input is completed, a first calculation mode is started.

iii) Next, in the first calculation mode, as shown in Step S103 in FIG. 3, the control section 11 acts as a first calculation section to determine a NaCl concentration for Na concentration) in total urine in one day when all the urine excreted by the subject in the one day is gathered into one volume, by performing conversion using a correlation (the correlation shown in FIG. 5A) stored in the correlation storage section 15, based on the NaCl concentration (Na concentration) in one urine 99 of the subject which is obtained via the data input section 12.

When the object to be converted is one associated with "second urine after wake-up", the correlation shown in FIG. 5B is accordingly used.

When the conversion is completed, a total urine amount acquirement mode is started.

iv) Next, in total urine amount acquirement mode, a total amount of urine excreted by the subject in one day is acquired based on conversion or a urine amount database as shown in Step S104 in FIG. 3.

In a first total urine amount acquirement method, a total amount of urine excreted by the subject in one day is acquired based on the urine amount database 15B.

Figure 4A:
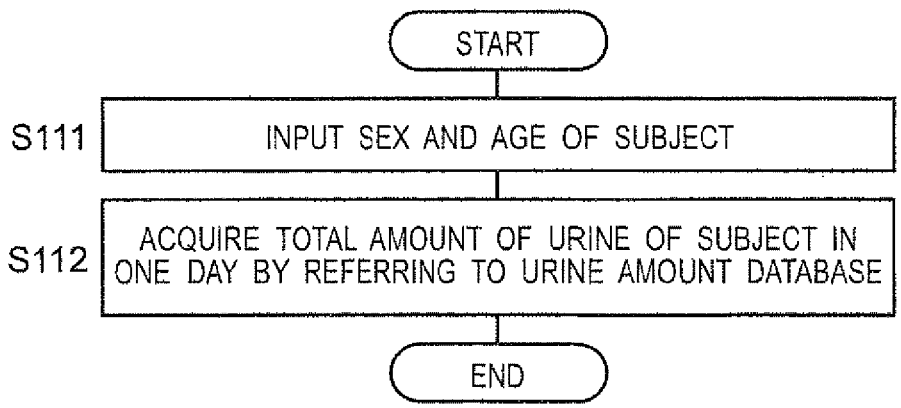
FIG. 4A is a view showing a flow for acquiring a total amount of urine excreted by a subject in one day based on a urine amount database.

In this case, first the user inputs the sex and age of the subject via the operation section 13 as shown in Step S111 in FIG. 4A.

Specifically, the control section 11 acts as a condition input section to display on the display section 18 options of "male" and "female" as sex. When the user rotates the scroll button 13A as these options are displayed, options of "male" and "female" are sequentially highlighted as a selection candidate. For example, when the user depresses the scroll button 13A while "male" is highlighted, "male" is input as sex of the subject. When input of sex is completed, a mode of input of "age" is started.

In the mode of input of "age", values indicating input candidates of age are displayed on the display section 18 in the ascending or descending manner when the user rotates the scroll button 13A. When the user depresses the scroll button 13A, a value displayed at this time is input as an age of the subject.

When input of age is completed, process proceeds to Step S112 in FIG. 4A, the control section 11 acts as a total urine amount acquirement section to acquire a total amount of urine excreted by the subject in one day, by referring to the urine amount data base 15B, based on the input sex and age.

In this case, for acquiring a total urine amount excreted by the subject in one day, the user (or subject) should only input several conditions. Thus, time and labor for measuring a urine amount by the subject can be saved.

In a second total urine amount acquirement method, unlike the first total urine amount acquirement method, a total amount of urine excreted by the subject in one day is acquired based on conversion.

In this case, a total amount of urine (e.g. 3.9 [L]) excreted by the subject over a sampling period of one day or longer (e.g. three days) is measured beforehand.

Figure 4B:
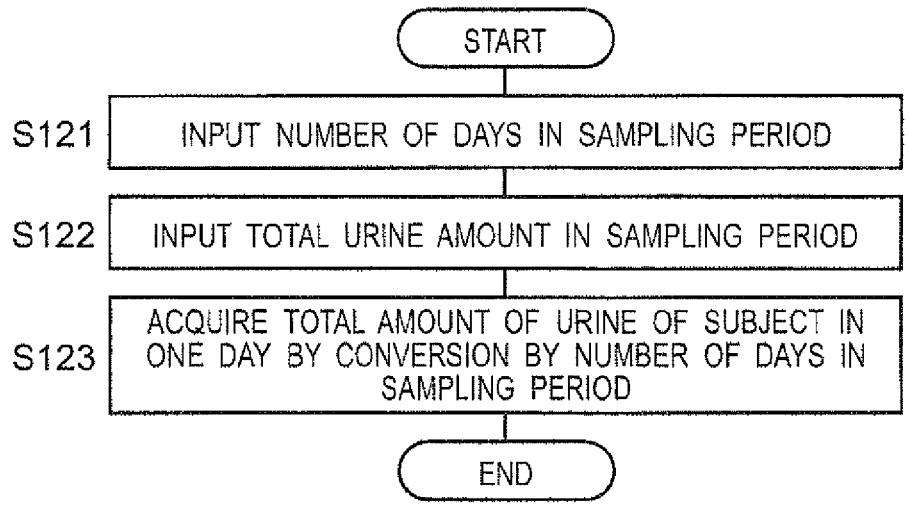
FIG. 4B is a view showing a flow for acquiring a total amount of urine excreted by a subject in one day based on conversion.

First, the user inputs a number of days in the sampling period (three days in the above example) and a total urine amount in the sampling period (3.9 [L] in the above example) via the operation section 13 as shown in Steps S121 and S122 in FIG. 4B. The specific input process via the operation section 13 is similar to the foregoing input process of "age".

Next, as shown in Step S123 in FIG. 4B, the control section 11 acts as a total urine amount acquirement section to determine a total amount of urine excreted by the subject in one day by a division: (total urine amount in sampling period)/(number of days in sampling period). In the above example, the total amount of urine excreted by the subject in one day is determined as 3.9 [L]/3 days=1.3 [L/day].

In this case, the subject should measure a urine amount only during a sampling period. Thus, time and labor for measuring a urine amount by the subject can be reduced when measurement is continued over a long period of time.

When acquirement of a total urine amount is completed, a second calculation mode is started.

Steps S101 to S103 and Step S104 in FIG. 3 may be replaced with each other.

v) Next, in the second calculation mode, as shown in Step S105 in FIG. 3, the control section 11 acts as a second calculation section to determine a NaCl excretion amount in total urine of the subject in one day by multiplying the NaCl concentration in total urine in one day, which is determined in Step S103, by the total urine amount in one day acquired in Step S104.

vi) Then, as shown in Step S106, the NaCl excretion amount obtained by conversion is stored in a calculation result storage section 16 in correspondence with a measurement date and time. At the same time, the NaCl excretion amount obtained by conversion is displayed on the display section 18.

vii) As shown in Step S107, the control section 11 acts as an advice section to select an advice appropriate to the NaCl excretion amount (salinity amount) obtained by conversion, by referring to the advice table 17 (FIG. 19), and display on the display section 18 the advice along with the NaCl excretion amount (salinity amount) obtained by conversion.

For example, if the NaCl excretion amount (salinity amount) is 2 g, the numerical value and the advice of "Ideal value" are displayed.

Thus, In the urine component analysis device 90, a total urine amount excreted by a subject in one day is acquired based on conversion or a database, and therefore time and labor for performing urine amount measurement by the subject can be reduced or saved. Moreover, a NaCl concentration in total urine in one day when all the urine excreted by the subject in the one day is gathered into one volume is determined by performing conversion using the correlation stored in the correlation storage section 15A, based on the input NaCl concentration in one urine of the subject. As a result, accuracy of calculation of a NaCl excretion amount can be enhanced.

Figure 7:
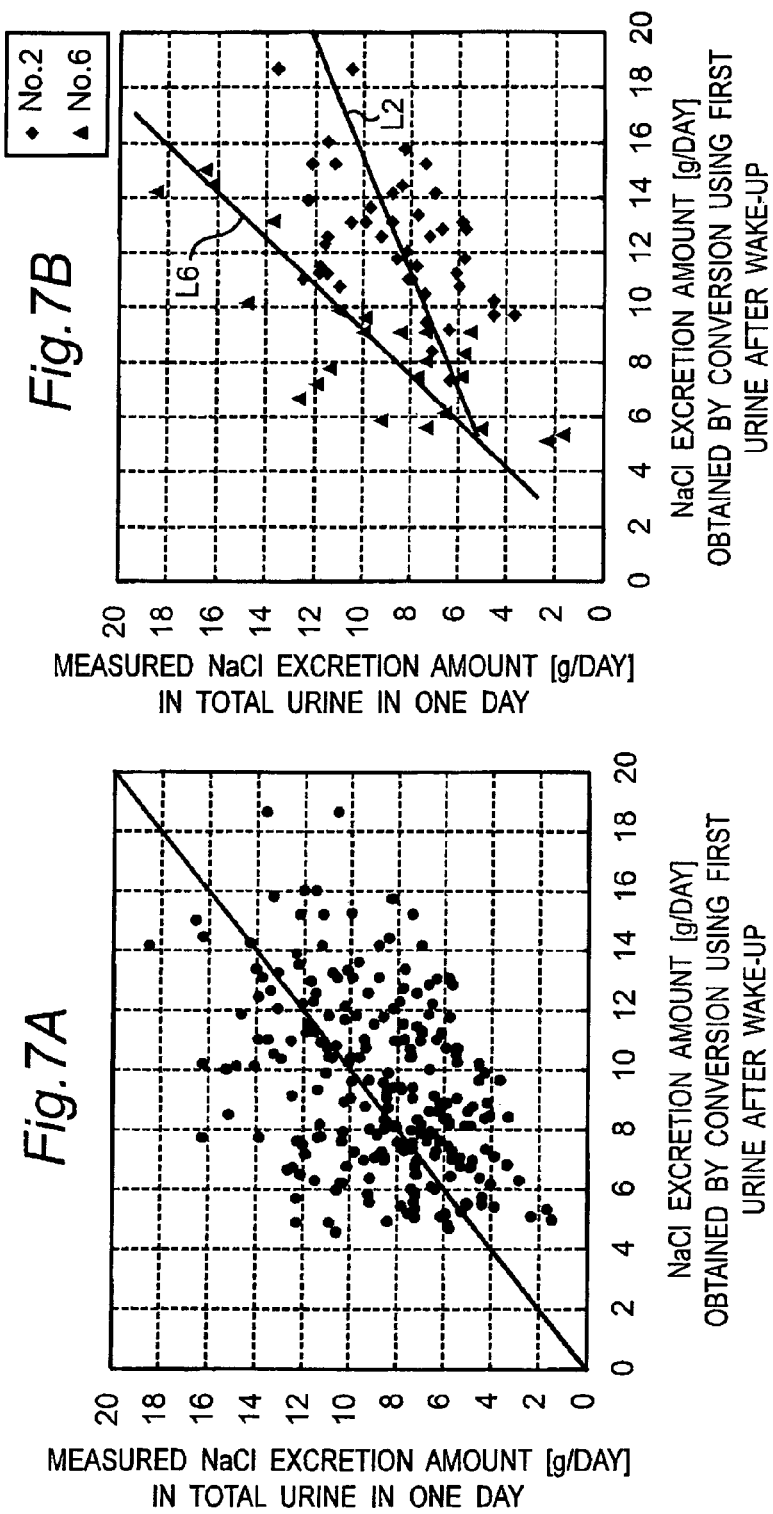
FIGS. 7A and 7B of FIG. 7 are views each showing a result of examining a NaCl excretion amount in total urine in one day, which is obtained, by conversion using one urine, by using a measured NaCl excretion amount in total urine in one day.

FIGS. 7A and 7B each show a result of examining a NaCl excretion amount in total urine in one day, which is obtained by conversion using one urine as described above, by using a measured NaCl excretion amount in total urine in one day, under the condition that a total amount of urine excreted by the subject in one day is acquired by the first total urine amount acquirement method (see urine amount database 15B). Specifically, FIG. 7A shows, for three or more subjects, a result of examining a state of correlation by matching a NaCl excretion amount ratio in total urine in one day (abscissa, unit:[g/day]), which is obtained by conversion using the first urine after wake-up, with a measured NaCl excretion amount in total urine in one day (ordinate, unit: [g/day]). In this result, a correlation is not so clearly shown because data of three or more subjects are not discriminated from one another. FIG. 7B shows, for subjects No. 2 and No. 6, results of determining a correlation coefficient by matching a NaCl excretion amount ratio in total urine in one day (abscissa x, unit: [g/day]), which is obtained by conversion using the first urine after wake-up, with a measured NaCl excretion amount in total urine in one day (ordinate y, unit: [g/day]). When the data of subject No. 2 is approximated by a straight line L2, the dispersion $R^2$ is 0.2204. When the data of subject No. 6 is approximated by a straight line L6, the dispersion $R^2$ is 0.6423. Thus, it has become apparent that when the data of subjects are discriminated from one another, a NaCl excretion amount in the urine excreted by the subject can be accurately determined.

FIG. 8A shows, for subject No. 2, a result of examining a daily NaCl excretion amount in total urine (data connected by a dashed line in the figure), which is obtained by conversion using one urine (first urine after wake-up), by using a measured daily NaCl excretion amount in total urine (data connected by a solid line in the figure), under the condition that the total urine amount in one day is acquired by the first total urine amount acquirement method (see urine amount database 153). FIG. 8B shows, for subject No. 6, a result of examining a daily NaCl excretion amount in total urine (data connected by a dashed line in the figure), which is obtained by conversion using one urine (first urine after wake-up), by using a measured daily NaCl excretion amount in total urine (data connected by a solid line in the figure), under the condition that the total urine amount in one day is acquired by the first total urine amount acquirement method (see urine amount database 15B).

In the result of examination for subject No. 6 in FIG. 8B, the daily NaCl excretion amount and the increase/decrease pattern thereof are substantially consistent between the converted value and the measured value. On the other hand, in the result of examination for subject No. 2 in FIG. 8A, the level of the converted value of the daily NaCl excretion amount is generally higher than the level of the measured value of the daily NaCl excretion amount. The reason for this may be that the actual total amount of urine excreted by subject No. 2 is shifted with respect to the total urine amount in one day acquired by referring to the urine amount database 15B for subject No. 2. However, the increase/decrease pattern of the daily NaCl excretion amount is substantially consistent between the converted value and the measured value. Therefore, the NaCl excretion amount obtained by conversion can be used as a criterion for improvement of life habits such as dietary life.

FIGS. 9A and 9B, 10A and 10B and 11A and 11B show, for the subject No. 2, results of examination when the method for acquiring a total amount of urine excreted by the subject in one day is variously changed.

Specifically, like FIG. 8A, FIG. 9A shows a result of examining a daily NaCl excretion amount in total urine, which is obtained by conversion using one urine, by using a measured daily NaCl excretion amount in total urine, under the condition that a total amount of urine excreted by the subject in one day is acquired by the first total urine amount acquirement method (see urine amount database 15B). FIG. 10A shows a result of examining a daily NaCl excretion amount in total urine, which is obtained by conversion using one urine, by using a measured daily NaCl excretion amount in total urine, under the condition that the total urine amount in one day is acquired by the second total urine amount acquirement method (converting the total urine amount during a sampling period by a number of days). FIG. 11A shows a result of examining a daily NaCl excretion amount in total urine, which is obtained by conversion using one urine, by using a measured daily NaCl excretion amount in total urine, under the condition that the total urine amount in one day (every day) is acquired by performing measurement. FIGS. 9B, 10B and 11B show average values obtained by averaging, respectively, the converted value and the measured value in FIGS. 9A, 10A and 11A for each week.

In FIGS. 9A and 9B, the level of the converted value of the NaCl excretion amount is generally higher than the level of the measured value of the NaCl excretion amount like the case described for FIG. 8A. In FIGS. 10A and 10B, the level of the converted value of the NaCl excretion amount is substantially consistent with the level of the measured value of the NaCl excretion, amount in general. The reason for this may be that for subject No. 2, the total urine amount in one day acquired by the first total urine amount acquirement method (see urine amount database 15B) is 1.3 [L], while the total urine amount in one day acquired by the second total urine amount acquirement method (converting the total urine amount during the sampling period is converted by a number of days) is 0.9 [L]. That is, it is considered that as accuracy of the total urine amount in one day acquired by the second total urine amount acquirement method is enhanced, accuracy of the NaCl excretion amount obtained by conversion is enhanced. When comparing FIGS. 10A and 10B with FIGS. 11A and 11B, the NaCl excretion amount obtained by conversion under the condition that the total urine amount in one day is obtained by the second total urine amount acquirement method (converting the total urine amount during the sampling period is converted by a number of days) is substantially comparable to the NaCl excretion amount obtained by conversion under the condition that the total urine amount in one day (every day) is acquired by performing measurement. Thus, it could be confirmed that an excretion amount of the specific component in total urine of the subject in one day can be accurately determined under the condition that the total urine amount in one day is acquired by the second total urine amount acquirement method (converting the total urine amount during a sampling period by a number of days).

For example, when the user continuously depresses the scroll button 13A for 3 or more seconds subsequent to turning on the power switch, the control section 11 may display on the display section 18 an option of which information of "urine specification", "sex", "age", "blood pressure", "BMI", "stature", "body weight", "season", "day", "atmospheric temperature" and "humidity" etc. is to be input. When the user rotates the scroll button 13A as these options are displayed, options of "urine specification", "sex", "age", "blood pressure" and "BMI" etc. are sequentially highlighted as a selection candidate. For example, when the user depresses the scroll button 13A while "blood pressure" is highlighted, a mode of input of "blood pressure" is started. In the mode of input of "blood pressure", values indicating input candidates of blood pressure (maximum blood pressure or minimum blood pressure) are displayed on the display section 18 in the ascending or descending manner when the user rotates the scroll button 13A. When the user depresses the scroll button 13A, a value displayed at this time is input as a blood pressure (maximum blood pressure or minimum blood pressure) of the subject. Other options such as BMI can be inputted in the same manner as in the case of the blood pressure.

In this case, when not only the advice appropriate to the salinity amount but also advices appropriate to the blood pressure and BMI are stored in the advice table 17 as shown in FIG. 20, a more appropriate advice can be given to the subject. In the example in FIG. 20, advices are stored while being classified in correspondence with a maximum blood pressure/minimum blood pressure of "less than 135/85 mmHg" and a BMI of "less than 25", a maximum blood pressure/minimum blood pressure of "135/85 mmHg or more" and a BMI of "25 or more" and a maximum blood pressure/minimum blood pressure of "135/25 mmHg or more" and a BMI of "less than 25" for each of salinity amount ranges of "0.0 to 3.0 g", "3.0 to 6.0 g", "6 to 7.5 g", "7.5 to 9.0 g" and "9.0 g or more".

For example, the advice of "Goal achieved for salinity reduction. You need weight reduction/exercise and medication" is stored for the salinity amount range of "3.0 to 6.0 g" and the maximum blood pressure/minimum blood pressure of "135/85 mmHg or more" and the BMI of "25 or more".

The advice of "Salinity amount so high. Take enough care of your dietary life. You need weight reduction/exercise and medication" is stored for the salinity amount range of "9.0 g or more" and the maximum blood pressure/minimum blood pressure of "135/85 mmHg or more" and the BMI of "25 or more".

When such an advice table is provided, a precise and more appropriate advice can be given to the subject.

When the user can operate the scroll button 13A to input "stature", "body weight", "season", "day", "atmospheric temperature" and "humidity" etc. in addition to "sex" and "age" of the subject, the urine amount database 15B may store data indicating a total urine amount per day of the human for each of conditions such as "stature", "body weight", "season", "day", "atmospheric temperature" and "humidity" etc. in addition to "sex" and "age". In this way, when a total urine amount of the subject in one day is acquired by the first total urine amount acquirement method (see urine amount database 15B), accuracy of the total urine amount in the one day can be enhanced. As a result, accuracy of the NaCl excretion amount obtained conversion can be enhanced.

According to the document (Katsumi Shibata, "Studies on Construction of Evidence for Modification of Diet Intake Standard of Japanese-Resolution of Balance between Micronutrient and Macronutrient Intakes-8. Variation in Human Urine Output by Age", 2007, General and Divisional Research Report, [Search: 25 May 2011], Internet <URL: http://www.shc.usp.ac.jp/shibata/H19-II-08.pdf>), "the daily urine amount of the healthy human was 671±223 ml/day for the elementary school student, 823±341 ml/day for the university student and 1731±610 ml/day for the aged"; and "when the daily urine amount is determined as a value per body weight, it is approximately 18.8 ml/kg for the elementary school student, 14.9 ml/kg for the university student and 29.0 ml/kg for the aged." The total urine amount per day of the human can be known in accordance with "age" or "body weight".

When the urine amount database 15B includes data indicating a total urine amount per day of the human by "season" and "day", a calendar section 40 that counts a date may be further provided as shown in FIG. 1, so that a season and a day when the subject excreted one urine or plural urines is automatically set by an output from the calendar section. In this way, the number of conditions to be input by the user is reduced to save time and labor of the user.

Second Embodiment

In the first embodiment described above, a NaCl concentration in total urine in one day is determined by performing conversion based on a NaCl concentration in one urine excreted by a subject, but the present invention is not limited thereto. A Na concentration (or NaCl concentration) in total urine in one day may be each determined by performing conversion based on a Na concentration (or Ncd concentration) in plural urines (two urines in this example) excreted by the subject over plural days.

In this case, as shown in, for example, FIG. 13A, data indicating a correlation between an average Na concentration obtained using two urines (first and second urines after wake-up) and a measured Na concentration in total urine in one day is stored in a correlation storage section 15. Specifically, FIG. 13A shows a case where a relationship between an average Na concentration obtained by averaging the measured Na concentration in the first urine after wake-up and a measured Na concentration in the second urine after wake-up (abscissa x, unit: [mmol/L]) and a measured Na concentration in total urine in one day (ordinate y, unit: [mmol/L]) is approximated by a straight line (shown by a solid line in FIG. 13A), and an expression of the straight line is stored as data indicating a correlation. In this case, it is shown that the correlation coefficient is r=0.82.

Alternatively, place of the correlation in FIG. 13A or in addition to the correlation in FIG. 13A, data indicating a correlation between an average Na concentration obtained using two urines (urine just before sleep and first urine after wake-up) and a measured Na concentration in total urine in one day is stored as shown in, for example, FIG. 13B. Specifically, FIG. 13B shows a case where a relationship between an average Na concentration obtained by averaging the measured Na concentration in the urine just before sleep and a measured Na concentration in the first urine after wake-up (abscissa x, unit: [mmol/L]) and a measured Na concentration in total urine in one day (ordinate y, unit: [mmol/L]) is approximated by a straight line (shown by a solid line in FIG. 13B), and an expression of the straight line is stored as data indicating a correlation. In this case, it is shown that the correlation coefficient is r=0.83.

Figure 12:
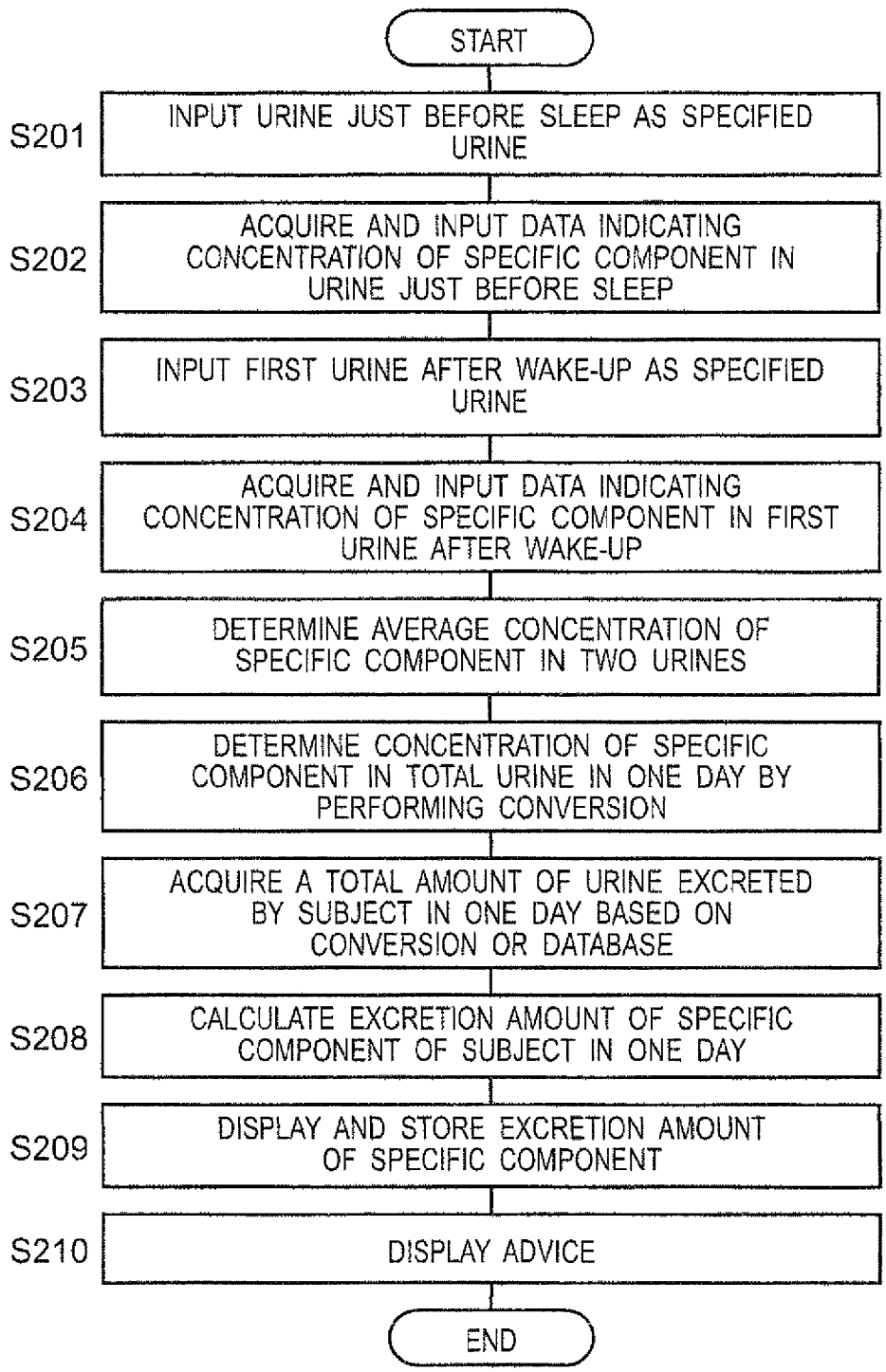
FIG. 12 is a view showing another example of an operational flow of the urine component analysis device.

In this case, a urine component analysis device 90 is operated under control by a control section 11 generally in accordance with a flow shown in, for example, FIG. 12.

i) First, for example when a user turns on a power switch (not illustrated), a first urine specification mode is started as shown in Step S201 in FIG. 12.

In this example, in the first urine specification mode, the user inputs, via an operation section 13, urine specification information indicating that urine to be measured is the urine just before sleep. When input of urine specification information is completed, a first urine measurement mode is started.

ii) in the first urine measurement mode, the user spritzes urine 99 on a sensor section 30 as shown in, for example, FIG. 2A, and depresses a scroll button 13A. Then, as shown in Step S202 in FIG. 12, the sensor section 30 acquires data indicating a Na concentration in one urine 99, and a data input section 12 inputs in real time the data indicating a Na concentration in this example.

In this example, a calculation mode is not started here, and the user turns off a power switch (not illustrated).

iii) Next, when the user turns on a power switch (not illustrated), a second urine specification mode is started as shown in Step S203 in FIG. 12.

In this example, in the second urine specification mode, the user inputs, via the operation section 13, urine specification information indicating that urine to be measured is the first urine after wake-up. When input of urine specification information is completed, a second urine measurement mode is started.

iv) In the second urine measurement mode, the user spritzes the urine 99 on a sensor section 30 again as shown in, for example, FIG. 2A, and depresses a scroll button 13A. Then, as shown in Step S204 in FIG. 12, the sensor section 30 acquires data indicating a Na concentration in one urine 99, and the data input section 12 inputs in real time the data indicating a Na concentration in this example.

When this second data input is completed, a first calculation mode is started.

v) In the first calculation mode, as shown in Step S205 in FIG. 12, the control section 11 acts as a first calculation section to determine an average Na concentration by averaging the Na concentration in two urines (urine just before sleep and first urine after wake-up in this example) excreted by the subject. That is, an average Na concentration is obtained by averaging the measured Na concentration in the urine just before sleep and a measured Na concentration the first urine after wake-up. The average Na concentration is an object to be converted.

vi) Next, as shown in Step S206 in FIG. 12, the control section 11 determine a Na concentration in total urine in one day when all the urine excreted by the subject in the one day is gathered into one volume, by performing conversion using a correlation (the correlation shown in FIG. 13B in this example) stored in a correlation storage section 15, based on the obtained average Na concentration.

When the object to be converted is one associated with "first urine after wake-up" and "second spot urine after wake-up", the correlation shown in FIG. 13A is accordingly used.

When the conversion is completed, a total urine amount acquirement mode is started.

vii) In the total urine amount acquirement mode, a total amount of urine excreted by the subject in one day is acquired based on conversion or a urine amount database as shown in Step S207 in FIG. 12.

In this example, second total urine amount acquirement method shown in FIG. 4B is used, i.e. a total amount of urine excreted by the subject in one day is acquired based on conversion.

In this case, a total amount of urine (e.g. 9.1 [L]) excreted by the subject over seven days as a sampling period is measured beforehand.

First, the user inputs a number of days in the sampling period (seven days in the above example) and a total urine amount in the sampling period (9.1 [L] in the above example) via the operation section 13 as shown in Steps S121 and S122 in FIG. 4B.

Next, as shown in Step S123 in FIG. 4B, the control section 11 acts as a total urine amount acquirement section to determine a total amount of urine excreted by the subject in one day by a division: (total urine amount in sampling period)/(number of days in sampling period). In the above example, the total amount of urine excreted by the subject in one day is determined as 9.1 [L]/7 days 1.3 [L/day].

In this case, the subject should measure a urine amount only during a sampling period. Thus, time and labor for measuring a urine amount by the subject can be reduced when measurement is continued over a long period of time.

When acquirement of a total urine amount is completed, a second calculation mode is started.

Steps S201 to S206 and Step S207 in FIG. 12 may be replaced with each other.

viii) In the second calculation mode, as shown in Step S208 in FIG. 12, the control section 11 acts as a second calculation section to determine a Ma excretion amount in total urine of the subject in one day by multiplying the Na concentration in total urine in one day, which is determined in Step S206, by the total urine amount in one day acquired in Step S207.

ix) Then, as shown in Step S209, the Na excretion amount obtained by conversion is stored in a calculation result storage section 16 in correspondence with a measurement date and time. At the same time, the Na excretion amount obtained by conversion is displayed on the display section 18.

x) As shown in Step S210, the control section 11 acts as an advice section to select an advice appropriate to the Na excretion amount (salinity amount) obtained by conversion, by referring to the advice table 17 (e.g. FIG. 19), and display on the display section 18 the advice along with the Na excretion amount (salinity amount) obtained by conversion.

FIG. 14B shows results of examining a Na excretion amount (abscissa) in total urine in one day, which is obtained by conversion using two urines (urine just before sleep and first urine after wake-up in this example), by using a measured Na excretion amount (ordinate) in total urine per day. For comparison, FIG. 14A shows results of examining a Na excretion amount (abscissa) in total urine in one day which is obtained by conversion using one spot urine (first urine after wake-up in this example), by using a measured Na excretion amount (ordinate) in total urine per day. Here, the correlation coefficient is r=0.69 in FIG. 14A, whereas the correlation coefficient is r=0.76 in FIG. 14B.

Thus, it has become apparent that when a Na concentration (or NaCl concentration) in total urine in one day is determined by performing conversion based on a Na concentration (or NaCl concentration) in two urines, a high correlation (correlation coefficient) is obtained between the converted value and the measured value, and resultantly a Na excretion amount in total urine of the subject in one day can be accurately determined.

When a Na concentration in one urine or an average Na concentration in two urines is used as an object to be converted, it is desirable that which is to be used should be determined in consideration of accuracy of conversion and ease of performing urine measurement by the subject. As for the order of accuracy, generally, a combination of "first urine after wake-up" and "second urine after wake-up" is ranked first, a combination of "urine just before sleep" and "first urine after wake-up" is ranked second, "second urine after wake-up" is ranked third, and "first urine after wake-up" is ranked fourth (one ranked first and one ranked second are comparable in accuracy). When the subject goes to work immediately after measuring a Na concentration in the first urine after wake-up at home, it is difficult in practice to measure a Na concentration in the "second urine after wake-up" at the workplace. Therefore, in this case, it is desirable to use a combination of "urine just before sleep" and "first urine after wake-up".

Third Embodiment

In the embodiments described above, an excretion amount of Na (or NaCl) in total urine in one day is determined by conversion, but an average value per day of the excretion amount of Na (or NaCl) may be determined based on a excretion amount of Na (or NaCl) obtained for each day.

Specifically, a control section 11 acts as a second calculation section to read a daily excretion amount of Na (or NaCl) stored in a calculation result storage section 16 and calculate an average value per day.

FIGS. 15A and 15B and FIGS. 16A and 16B each show a result of examining an average value per day of the Na excretion amount obtained for each day, by using an average value per day of the measured Na excretion amount in total urine, while variously changing a period (number of days) d for which the average value is calculated.

Specifically, FIG. 15A shows a result of examining a Na excretion amount in total urine in one day (d=1), which is obtained by conversion using one urine (first urine after wake-up), by using a measured Na excretion amount in total urine in one day. FIG. 15B shows a result of examining an average value over three days (d=3) of the Na excretion amount in total urine in one day, which is obtained by conversion using one urine (first urine after wake-up), by using an average value per day of the measured Na excretion amount in total urine over three days. FIG. 16A shows a result of examining an average value over five days (d=5) of the Na excretion amount in total urine in one day, which is obtained by conversion using one urine (first urine after wake-up), by using an average value per day of the measured Na excretion amount in total urine over five days. FIG. 16B shows a result of examining an average value over seven days (d=7) of the Na excretion amount in total urine in one day, which is obtained by conversion using one urine (first urine after wake-up), by using an average value per day of the measured Na excretion amount in total urine over seven days. Here, the correlation coefficient is r=0.69 in FIG. 15A, whereas the correlation coefficient is r=0.79 in FIG. 15B, the correlation coefficient is r=0.81 in FIG. 16A, and the correlation coefficient is r=0.83 in FIG. 16B.

Thus, it has become apparent that when the period (number of days) d is increased, a high correlation (correlation coefficient) is obtained between the converted value and the measured value, and resultantly a Na excretion amount in total urine of the subject in one day can be accurately determined.

Similarly, FIGS. 17A and 17B and FIGS. 18A and 18B each show a result of examining an average value per day of the Na excretion amount obtained for each day, by using an average value per day of the measured Na excretion amount in total urine, while variously changing a period (number of days) d for which the average value is calculated.

Specifically, FIG. 17A shows a result of examining a Na excretion amount in total urine in one day (d=1), which is obtained by conversion using two urines (urine just before sleep and first urine after wake-up), by using a measured Na excretion amount in total urine in one day. FIG. 17B shows a result of examining an average value over three days (d=3) of the Na excretion amount in total urine in one day, which is obtained by conversion using two urines (urine just before sleep and first urine after wake-up), by using an average value per day of the measured Na excretion amount in total urine over three days. FIG. 18A shows a result of examining an average value over five days (d=5) of the Na excretion amount in total urine in one day, which is obtained by conversion using two urines (urine just before sleep and first urine after wake-up), by using an average value per day of the measured Na excretion amount in total urine over five days. FIG. 18B shows a result of examining an average value over seven days of the Na excretion amount in total urine in one day, which is obtained by conversion using two urines (urine just before sleep and first urine after wake-up), by using an average value per day of the measured Na excretion amount in total urine over seven days (d=7). Here, the correlation coefficient is r=0.76 in FIG. 17A, whereas the correlation coefficient is r=0.86 in FIG. 17B, the correlation coefficient is r=0.90 in FIG. 18A, and the correlation coefficient is r=0.91 in FIG. 18B.

Also in this case, it has become apparent that when the period (number of days) d is increased, a high correlation (correlation coefficient) is obtained between the converted value and the measured value, and resultantly a Na excretion amount in total urine of the subject in one day can be accurately determined.

As a whole, for the number of times and the period (number of days) in which data about a concentration of a specific component the urine excreted by the subject is measured, one urine or plural urines per day may be measured ever plural days. When the number of measurements and the number of measurement days are increased, accuracy of the Na excretion amount (or NaCl excretion amount) obtained by conversion can be enhanced. The subject is not required to perform measurement every day during the measurement period. For example, measurement may be performed only six times during a measurement period of seven days.

In the embodiments described above, the user inputs, via an operation section 13, urine specification information indicating whether urine to be measured is the first urine after wake-up or the second urine after wake-up or the urine just before sleep, but the present invention is not limited thereto. The control section 11 may act as a urine determination section to determine whether the one urine or the plural urines excreted by the subject are the first urine after wake-up or the second urine after wake-up or the urine just before sleep, in accordance with a time at which data about a Na concentration (NaCl concentration) is input. In this way, time and labor of inputting urine specification information by the user can be saved.

In the embodiments described above, the display section 18 is provided as a notification section, but the present invention is not limited thereto. For example, the notification section may include a speaker in addition to the display section 18 or in place of the display section 18. In this case, the user can be notified of a Na excretion amount (NaCl excretion amount) calculated by the control section 11 and an advice appropriate to the Na excretion amount (or NaCl excretion amount) by voice through the speaker.

Fourth Embodiment

Figure 21:
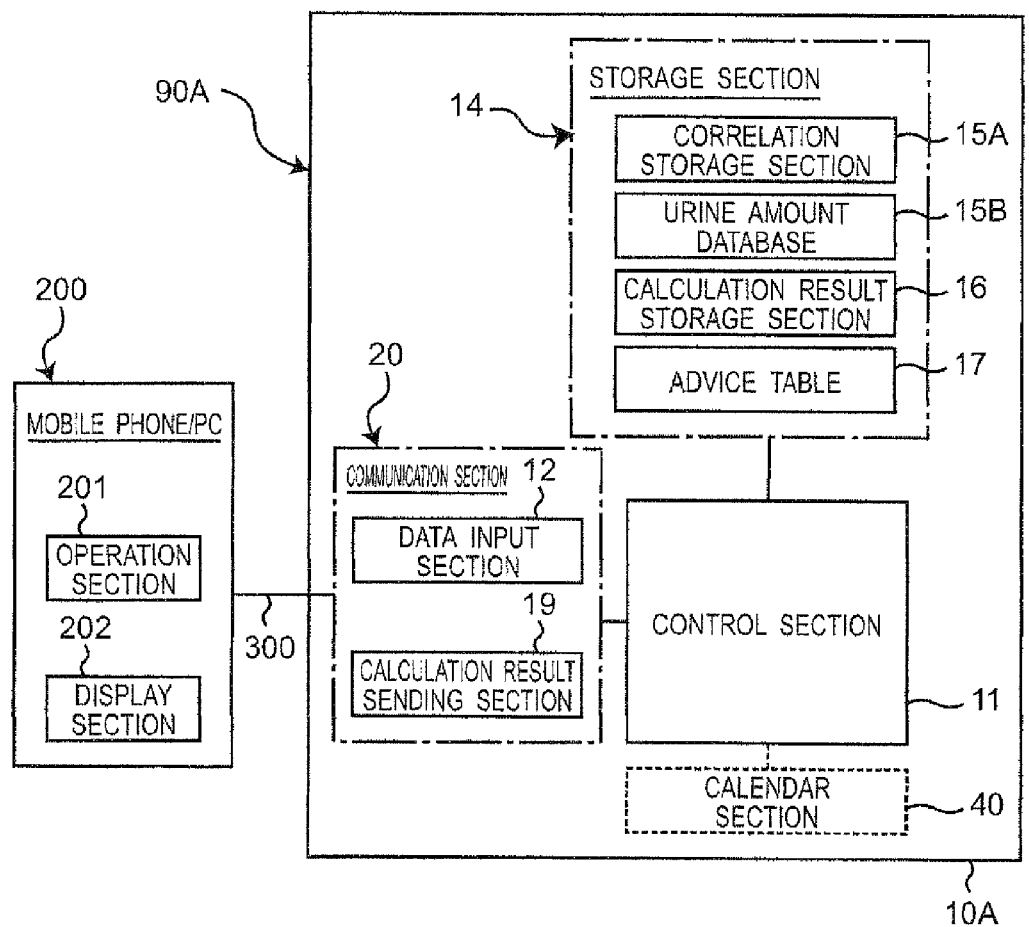
FIG. 21 is a view showing a block configuration of a urine component analysis device of another embodiment of the present invention.

FIG. 21 shows a block configuration of a urine component analysis device (denoted by symbol 90A as a whole) of another embodiment of the present invention. For easy understanding, constituent elements same as those in FIG. 1 are given the same symbols, and duplicated explanations are omitted.

The urine component analysis device 90A includes at least a housing 10A, a control section 11 mounted and stored in the housing 10, a storage section 14 and a communication section 20.

In this example, the housing 10A is formed as a tower type housing to be placed on a desk or a floor.

The communication section 20 includes a data input section 12 and a calculation result sending section 19. The communication section 20 is connected via a wireless or wired communication line 300 to a mobile phone or personal computer (PC) 200 present outside the housing 10A. In this example, a subject as a user uses the mobile phone or PC 200 by operating an operation section 201 (keyboard, ten key and mouse etc.).

The data input section 12 receives data about a concentration of a specific component (Na concentration or NaCl concentration in this example) in the urine excreted by the subject via the communication line 300 from the mobile phone or PC 200, and inputs the data.

The calculation result sending section 19 outputs a calculation result (Na excretion amount or NaCl excretion amount in this example) calculated by the control section 11 to the mobile phone or PC 200 via the communication line 300.

As a result, the urine component analysis device 90A is formed as a server type urine component analysis device that performs input of data and output of a calculation result via the wireless or wired communication line 300.

For example, when the server type urine component analysis device 90A is used, the subject as a user at a remote location away from the housing 10A acquires data about a Na concentration (or NaCl concentration) by a commercially available sensor etc. The data is input by the data input section 12 via the wireless or wired communication line 300 from the mobile phone or PC 200 which is operated by the subject. At the same time, the subject inputs, via the operation section 201 of the mobile phone or PC 200, urine specification information indicating whether urine to be measured is the first urine after wake-up or the second urine after wake-up or the urine just before sleep. The urine specification information is input from the mobile phone or PC 200 to the control section 11 via the wireless or wired communication line 300 and via the communication section 20. As a result, a Na excretion amount (or NaCl excretion amount) in total urine in one day when all the urine excreted by the subject in the one day is gathered into one volume is calculated by the control section 11. The Na excretion amount (or NaCl excretion amount) calculated by the calculation section 11 is output, together with an advice appropriate to the Na excretion amount (or NaCl excretion amount), to the mobile phone or PC 200 of the subject at a remote location away from the housing 10A via the wireless or wired communication line 300 by the calculation result sending section 19. As a result, the subject can know the Na excretion amount (or NaCl excretion amount) calculated by the control section 11 and the advice appropriate to the Na excretion amount (or NaCl excretion amount), through a display section (LCD etc.) 202 of the mobile phone or PC 200, at a location where the subject is present.

Thus, the server type urine component analysis device 90A can be easily used by a user at a remote location away from the housing 10A.

In the embodiments described above, the specific component in urine to be determined by conversion is sodium (Na) or sodium chloride (NaCl), but the present invention is not limited thereto. The specific component may be one of, for example, sodium, potassium, calcium and glucose. When these components are obtained, an advice useful for improvement of life habits, such as dietary life, of the subject can be given. Particularly, when the specific component is sodium, the excretion amount of the specific component obtained by conversion corresponds to an amount salinity sodium chloride) taken by the subject in one day. Therefore, the excretion amount of the specific component can be used as information for hypertension of the subject.

As described above, a urine component analysis device of the present invention comprises:

a correlation storage section which stores data indicating a correlation between a concentration of a specific component in one urine excreted by a human and a concentration of the specific component in total urine in one day when all the urine excreted by the human in the one day is gathered into one volume;

a total urine amount acquirement section which acquires a total amount of urine excreted by a subject in one day based on conversion or a database;

a data input section which inputs data indicating a concentration of the specific component in one urine excreted by the subject;

a first calculation section which determines a concentration of the specific component in total urine in one day when all the urine excreted by the subject in the one day is gathered into one volume, by performing conversion using the correlation stored in the correlation storage section, based on the concentration of the specific component in the one urine of the subject obtained via the data input section; and a second calculation section which calculates an excretion amount of the specific component in the total urine of the subject in the one day by multiplying the concentration of the specific component in the total urine in the one day, which is determined by the first calculation section, by the total urine amount in the one day acquired by the total urine amount acquirement section.

According to the urine component analysis device of the present invention, the correlation storage section stores data indicating a correlation between a concentration of a specific component in one urine excreted by a human and a concentration of the specific component in total urine in one day when all the urine excreted by the human in the one day is gathered into one volume. The total urine amount acquirement section acquires a total amount of urine excreted by a subject in one day based on conversion or a database. The data input section inputs data indicating a concentration of the specific component in one urine excreted by the subject. The first calculation section determines a concentration of the specific component in total urine in one day when all the urine excreted by the subject in the one day is gathered into one volume, by performing conversion using the correlation stored in the correlation storage section, based on the concentration of the specific component in the one urine of the subject obtained via the data input section. Furthermore, The second calculation section calculates an excretion amount of the specific component in the total urine of the subject in the one day by multiplying the concentration of the specific component in the total urine in the one day, which is determined by the first calculation section, by the total urine amount in the one day acquired by the total urine amount acquirement section.

Here, in the urine component analysis device, the total urine amount acquirement section acquires a total urine amount excreted by a subject in one day, based on conversion or a database, and therefore time and labor for performing urine amount measurement by the subject can be reduced or saved. Therefore, an excretion amount of a specific component in total urine of the subject in one day can be easily and conveniently determined. Moreover, in the urine component analysis device, the first calculation section determines by conversion a concentration of the specific component in total urine in one day when all the urine excreted by the subject in the one day is gathered into one volume, by performing conversion using the correlation stored in the correlation storage section, based on the concentration of the specific component in the one urine of the subject, which is obtained via the data input section. As a result, accuracy of calculation of an excretion amount of the specific component in the total urine of the subject in the one day by the second calculation section can be enhanced.

In the urine component analysis device of one embodiment, the correlation storage section stores data indicating a correlation between an average concentration obtained by averaging the concentration of the specific component in plural urines excreted by the human over one day or plural days and a concentration of the specific component in total urine in one day or plural days when all the urine excreted by the human over the one day or the plural days is gathered into one volume;

the total urine amount acquirement section acquires a total amount of urine excreted by the subject in one day or plural days based on conversion or a database;

the data input section inputs data indicating a concentration of the specific component in plural urines excreted by the subject over one day or plural days;

the first calculation section obtains an average concentration by averaging the concentration of the specific component in the plural urines excreted by the subject over one day or plural days, and defines the average concentration as an object for the conversion; and the second calculation section calculates an excretion amount of the specific component of the subject over the one day or the plural days by multiplying the concentration of the specific component in the total urine in the one day, which is determined by the first calculation section, by the total urine amount in the one day or the plural days acquired by the total urine amount acquirement section.

In the urine component analysis device of this embodiment, the correlation storage section stores data indicating a correlation between an average concentration obtained by averaging the concentration of the specific component in plural urines excreted by the human over one day or plural days and a concentration of the specific component in total urine in one day or plural days when all the urine excreted by the human over the one day or the plural days is gathered into one volume. The total urine amount acquirement section acquires a total amount of urine excreted by the subject in one day or plural days based on conversion or a database. The data input section inputs data indicating a concentration of the specific component in plural urines excreted by the subject over one day or plural days. The first calculation section obtains an average concentration by averaging the concentration of the specific component in the plural urines excreted by the subject over one day or plural days, and defines the average concentration as an object for the conversion. Furthermore, the second calculation section calculates an excretion amount of the specific component of the subject over the one day or the plural days by multiplying the concentration of the specific component in the total urine in the one day, which is determined by the first calculation section, by the total urine amount in the one day or the plural days acquired by the total urine amount acquirement section. In this case, accuracy of the calculated excretion amount of the specific component is enhanced.

In the urine component analysis device of one embodiment, the second calculation section calculates an average value per day of the excretion amount of the specific component based on an excretion amount of the specific component obtained for each day.

In the urine component analysis device of this embodiment, the second calculation section calculates an average value per day of the excretion amount of the specific component based on an excretion amount of the specific component obtained for each day. Therefore, an excretion amount of the specific component in the urine of the subject per day is accurately calculated.

In the urine component analysis device of one embodiment, the one urine or the plural urines are one of first urine after wake-up, second urine after wake-up and urine just before sleep; and the first calculation section can uses the correlation corresponding to whether the one urine or the plural urines are the first urine after wake-up or the second urine after wake-up or the urine just before-sleep.

In this specification, the "urine just before sleep" refers to the last one urine excreted by the subject before sleep.

In the urine component analysis device of this embodiment, the one urine or the plural urines are one of first urine after wake-up, second urine after wake-up and urine just before sleep. The first calculation section can uses the correlation corresponding to whether the one urine or the plural urines are the first urine after wake-up or the second urine after wake-up or the urine just before sleep. In this case, accuracy of the calculated excretion amount of the specific component is further enhanced.

The urine component analysis device of one embodiment further comprises a urine specification section which inputs information indicating whether the one urine or the plural urines excreted by the subject are the first urine after wake-up or the second urine after wake-up or the urine just before sleep.

In the urine component analysis device of this embodiment, a user (may be identical to the subject or may be one who operates the device for the subject) can input, via a urine specification section, information indicating whether the one urine or the plural urines excreted by the subject are the first urine after wake-up or the second urine after wake-up or the urine just before sleep. By input of the information, whether the one urine or the plural urines excreted by the subject are the first urine after wake-up or the second urine after wake-up or the urine just before sleep is specified. As a result, among correlations stored in the correlation storage section, the first calculation section can select and use a correlation corresponding to whether the one urine or the plural urines are the first urine after wake-up or the second urine after wake-up or the urine just before sleep.

In the urine component analysis device of one embodiment, the data input section inputs data about the specific component in real time. The urine component analysis device further comprises a urine determination section which determines whether the one urine or the plural urines excreted by the subject are the first urine after wake-up or the second urine after wake-up or the urine just before sleep, in accordance with a time at which the data about a concentration of the specific component is input.

in this specification, the "data about concentration of the specific component" includes data indicating a concentration of the specific component, and may further include data for correcting the concentration.

In the urine component analysis device of this embodiment, the data input section inputs data about the specific component in real time. The urine determination section determines whether the one urine or the plural urines excreted by the subject are the first urine after wake-up or the second urine after wake-up or the urine just before sleep, in accordance with a time at which the data about a concentration of the specific component is input. By this result of determination, whether the one urine or the plural urines excreted by the subject are the first urine after wake-up or the second urine after wake-up or the urine just before sleep is specified. As a result, among correlations stored in the correlation storage section, the first calculation section can select and use a correlation corresponding to whether the one urine or the plural urines are the first urine after wake-up or the second urine after wake-up or the urine just before sleep.

In the urine component analysis device of one embodiment, the total urine amount in the one day or the plural days, which is acquired by the total urine acquirement section, is an amount obtained by measuring a total amount of urine excreted by the subject over a sampling period of one day or longer, and converting the total urine amount in the sampling period by a number of days.

Here, "conversion by a number of days" means that a total urine amount in a sampling period is multiplied by a ratio of (number of days in the one day or the plural days)/number of days in sampling period).

In the urine component analysis device of this embodiment, the total urine amount in the one day or the plural days, which is acquired by the total urine acquirement section, is an amount obtained by measuring a total amount of urine excreted by the subject over a sampling period of one day or longer, and converting the total urine amount in the sampling period by a number of days. Therefore, the subject should measure a urine amount only during a sampling period. Thus, time and labor for measuring a urine amount by the subject can be reduced.

The urine component analysis device of one embodiment further comprises a condition input section which inputs at least one condition of sex, age, stature and body weight of the subject and season, day, atmospheric temperature and humidity when the subject excretes the one urine or the plural urines. The total urine amount acquirement section acquires a total amount of urine excreted by the subject in one day, by referring to a predetermined database storing a total urine amount per day of a human, based on the condition input via the condition input section.

In the urine component analysis device of this embodiment, the condition input section inputs at least one condition of sex, age, stature and body weight of the subject and season, day, atmospheric temperature and humidity when the subject excretes the one urine or the plural urines. The total urine amount acquirement section acquires a total amount of urine excreted by the subject in one day, by referring to a predetermined database storing a total urine amount per day of a human, based on the condition input via the condition input section. Therefore, for acquiring a total urine amount excreted by the subject in one day, the user (or subject) should only input several conditions. Thus, time and labor for measuring a urine amount by the subject can be saved.

The urine component analysis device of one embodiment further comprises a calendar section which counts a date.

The season and day when the subject excretes the one urine or the plural urines are set by the output of the calendar section.

The urine component analysis device of this embodiment includes a calendar section which counts a date. Therefore, a season and day when the subject excretes the one urine or the plural urines can be automatically set by an output from the calendar section. In this way, the number of conditions to be input by the user via the condition input section is reduced to save time and labor of the user.

The urine component analysis device of one embodiment further comprises a sensor section which comes into contact with urine excreted by the subject to acquire data about a concentration of the specific component.

In the urine component analysis device of this embodiment, the sensor section comes into contact with urine excreted by the subject to acquire data about a concentration of the specific component. The concentration of the specific component acquired by the sensor section is input by the data input section to become an object to be converted by the first calculation section.

The urine component analysis device of one embodiment further comprises a calculation result storage section which stores an excretion amount of the specific component calculated by the second calculation section.

In the urine component analysis device of this embodiment, an excretion amount of the specific component calculated by the second calculation section is stored in the calculation result storage section. Therefore, the user can easily know the excretion amount of the specific component in the total urine of the subject in the one day by reading the contents of the calculation result storage section. Particularly, when the excretion amount of the specific component in total urine of the subject in one day is daily stored in the calculation result storage section, the user can easily know a tendency of daily change in excretion amount of the specific component.

The urine component analysis device of one embodiment further comprises a notification section which gives a notification of excretion amount of the specific component calculated by the second calculation section.

In the urine component analysis device of this embodiment, the notification section gives a notification of excretion amount of the specific component calculated by the second calculation section. Therefore, the user can easily know the excretion amount of the specific component in total urine of the subject in the one day by receiving a notification from the notification section.

The urine component analysis device of one embodiment further comprises a housing including at least the correlation storage section, the total urine amount acquirement section, the data input section, the first calculation section and the second calculation section. The sensor section is attached to the housing so as to be projected to outside from the housing.

The urine component analysis device of this embodiment comprises a housing including at least the correlation storage section, the total urine amount acquirement section, the data input section, the first calculation section and the second calculation section. The sensor section is attached to the housing so as to be projected to outside from the housing. Accordingly, a hand-held type urine component analysis device that is used by the user with the housing held in the hand is constituted.

For example, when the hand-held type urine component analysis device is used, urine is spritzed on the sensor section with the housing held in the hand when the subject as a user discharges the urine. In this way, the sensor section comes into contact with urine excreted by the subject to acquire data about a concentration of the specific component.

Alternatively, when the subject as a user discharges urine, the subject may collect a part of one urine in a disposable paper cup, and immerse the sensor section in the urine in the paper cup with the housing held in the hand.

Alternatively, when the subject as a user discharges urine, the subject may infiltrate a part of one urine into a sheet of toilet paper, and bring the sensor section into contact with the urine infiltrated in the sheet of toilet paper with the housing held in the hand.

In any case, according to the hand-held type urine component analysis device, a calculation result is obtained by simple operations.

The urine component analysis device of one embodiment further comprises a housing including at least the correlation storage section, the total urine amount acquirement section, the data input section, the first calculation section and the second calculation section. The data input section inputs data about a concentration of the specific component via a wireless or wired communication line. The housing further includes a calculation result sending section which sends an excretion amount of the specific component calculated by the second calculation section to outside of the housing via a wireless or wired communication line.

In the urine component analysis device of this embodiment comprises a housing including at least the correlation storage section, the total urine amount acquirement section, the data input section, the first calculation section and the second calculation section. The data input section inputs data about a concentration of the specific component via a wireless or wired communication line. The housing further includes a calculation result sending section which sends an excretion amount of the specific component calculated by the second calculation section to outside of the housing via a wireless or wired communication line. Accordingly, a server type urine component analysis device that performs input of data and output of a calculation result via a wireless or Wired communication line can be formed.

For example, when the server type urine component analysis device is used, the subject as a user at a remote location away from the housing acquires data about a concentration of the specific component by means such as a sensor etc. The data is input by the data input section via a wireless or wired communication line. As a result, an excretion amount of the specific component in total urine of the subject in one day is calculated by the second calculation section. The excretion amount of the specific component calculated by the second calculation section is output to the subject at a remote location away from the housing via the wireless or wired communication line by the calculation result sending section. As a result, the subject can know the excretion amount of the specific component calculated by the second calculation section, through a display screen of, for example, a personal computer, at a location where the subject is present.

Thus, the server type urine component analysis device can be easily used by a user at a remote location away from the housing.

In the urine component analysis device of one embodiment, the specific component is one of sodium, potassium, calcium and glucose.

In the urine component analysis device of this embodiment, the specific component is one of sodium, potassium, calcium and glucose. Therefore, the excretion amount of the specific component in total urine of the subject in the one day, which is obtained by the calculation section, can be used as useful information for improving the dietary life of the subject. Particularly, when the specific component is sodium, the excretion amount of the specific component in total urine in the one day calculated by the second calculation section corresponds to an amount of salinity (sodium chloride) taken by the subject in the one day. Therefore, the excretion amount of the specific component can be used as information about hypertension of the subject.

The urine component analysis device of one embodiment further comprises:

an advice table which stores an excretion amount of salinity as the specific component in correspondence with an advice appropriate to the excretion amount of salinity for the subject; and an advice section which selects an advice appropriate to the excretion amount of salinity as the specific component, which is calculated by the second calculation section, by referring to the advice table.

Here, for example, the "advice" may be an advice about hypertension of the subject.

The urine component analysis device this embodiment comprises an advice table which stores an excretion amount of salinity as the specific component in correspondence with an advice appropriate to the excretion amount of salinity for the subject. The advice section selects an advice appropriate to the excretion amount of salinity as the specific component, which is calculated by the second calculation section, by referring to the advice table. Therefore, for example, an advice about hypertension of the subject can be given in accordance with the excretion amount of salinity as the specific component, which is calculated by the second calculation section.

In another aspect, the urine component analysis method of the present invention comprises:

storing in a predetermined storage section data indicating a correlation between a concentration of a specific component in one urine excreted by a human and concentration, of the specific component in total urine in one day when all the urine excreted by the human in the one day is gathered into one volume;

acquiring a total amount of urine excreted by a subject in one day based on conversion or a database, and inputting data indicating a concentration of the specific component in one urine excreted by the subject;

determining a concentration of the specific component in total urine in one day when all the urine excreted by the subject in the one day is gathered into one volume, by performing conversion using the correlation stored in the storage section, based on the input concentration of the specific component in the one urine of the subject; and calculating an excretion amount of the specific component in the total urine of the subject in the one day by multiplying the determined concentration of the specific component in the total urine in the one day by the total urine amount in the one day acquired based on conversion or a database.

According to the urine component analysis method of the present invention, a total urine amount excreted by a subject in one day is acquired based on conversion or a database, and therefore time and labor for performing urine amount measurement by the subject can be reduced or saved. Therefore, an excretion amount of a specific component in total urine of the subject in one day can be easily and conveniently determined. Moreover, in the urine component analysis method, a concentration of the specific component in total urine in one day when all the urine excreted by the subject in the one day is gathered into one volume is determined by performing conversion using the correlation stored in the correlation storage section, based on the concentration of the specific component in the one urine of the subject, which is input. As a result, accuracy of calculation of an excretion amount of the specific component can be enhanced.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A urine component analysis device for determining an excretion amount of a specific component in total urine excreted by a subject in one day, the urine component analysis device comprising:

a housing;

a display section mounted and stored in the housing;

a sensor that is attached to the housing so as to project from one end of the housing;

a correlation storage section comprising a non-transitory memory, mounted in the housing, which stores data indicating a correlation between a concentration of the specific component in one urine excreted by a human and a concentration of the specific component in total urine in one day when all the urine excreted by the human in the one day is gathered into one volume;

a total urine amount acquirement section, executed by a processor mounted in the housing, which acquires a total amount of urine excreted by the subject in one day based on conversion or a database;

a data input section, mounted in the housing, which receives data acquired by the sensor and indicating a concentration of the specific component in one urine excreted by the subject;

a first calculation section comprising a processor, mounted in the housing, that is programmed with instructions to determine a concentration of the specific component in total urine in one day when all the urine excreted by the subject in the one day is gathered into one volume, by performing conversion using the correlation stored in the correlation storage section, based on the concentration of the specific component in the one urine of the subject obtained via the data input section; and a second calculation section executed by the processor, mounted in the housing, that is also programmed with instructions to calculate an excretion amount of the specific component in the total urine of the subject in the one day by multiplying the concentration of the specific component in the total urine in the one day, which is determined by the first calculation section, by the total urine amount in the one day acquired by the total urine amount acquirement section, wherein the display section provides a notification of the excretion amount of the specific component calculated by the second calculation section.

2. The urine component analysis device according to claim 1, wherein the correlation storage section stores data indicating a correlation between an average concentration obtained by averaging the concentration of the specific component in plural urines excreted by the human over one day or plural days and a concentration of the specific component in total urine in one day or plural days when all the urine excreted by the human over the one day or the plural days is gathered into one volume;

the total urine amount acquirement section acquires a total amount of urine excreted by the subject in one day or plural days based on conversion or a database;

the data input section inputs data indicating a concentration of the specific component in plural urines excreted by the subject over one day or plural days;

the first calculation section obtains an average concentration by averaging the concentration of the specific component in the plural urines excreted by the subject over one day or plural days, and defines the average concentration as an object for the conversion; and the second calculation section calculates an excretion amount of the specific component of the subject over the one day or the plural days by multiplying the concentration of the specific component in the total urine in the one day, which is determined by the first calculation section, by the total urine amount in the one day or the plural days acquired by the total urine amount acquirement section.

3. The urine component analysis device according to claim 2,
wherein the second calculation section calculates an average value per day of the excretion amount of the specific component based on an excretion amount of the specific component obtained for each day.

4. The urine component analysis device according to claim 2,
wherein the one urine or the plural urines are one of first urine after wake-up, second urine after wake-up and urine just before sleep; and
the first calculation section can uses the correlation corresponding to whether the one urine or the plural urines are the first urine after wake-up or the second urine after wake-up or the urine just before sleep.

5. The urine component analysis device according to claim 4,
wherein the urine component analysis device comprises a urine specification section which inputs information indicating whether the one urine or the plural urines excreted by the subject are the first urine after wake-up or the second urine after wake-up or the urine just before sleep.

6. The urine component analysis device according to claim 4,
wherein the data input section inputs data about the specific component in real time; and
the urine component analysis device comprises a urine determination section which determines whether the one urine or the plural urines excreted by the subject are the first urine after wake-up or the second urine after wake-up or the urine just before sleep, in accordance with a time at which the data about a concentration of the specific component is input.

7. The urine component analysis device according to claim 2,
wherein the total urine amount in the one day or the plural days, which is acquired by the total urine acquirement section, is an amount obtained by measuring a total amount of urine excreted by the subject over a sampling period of one day or longer, and converting the total urine amount in the sampling period by a number of days.

8. The urine component analysis device according to claim 2,
wherein the urine component analysis device comprises a condition input section which inputs at least one condition of sex, age, stature and body weight of the subject and season, day, atmospheric temperature and humidity when the subject excretes the one urine or the plural urines; and
the total urine amount acquirement section acquires a total amount of urine excreted by the subject in one day, by referring to a predetermined database storing a total urine amount per day of a human, based on the condition input via the condition input section.

9. The urine component analysis device according to claim 8,
wherein the urine component analysis device comprises a calendar section which counts a date; and
the season and day when the subject excretes the one urine or the plural urines are set by the output of the calendar section.

10. The urine component analysis device according to claim 1, wherein the urine component analysis device comprises a calculation result storage section which stores an excretion amount of the specific component calculated by the second calculation section.

11. The urine component analysis device according to claim 1, wherein
the data input section inputs data about a concentration of the specific component via a wireless or wired communication line; and
the housing further includes a calculation result sending section which sends an excretion amount of the specific component calculated by the second calculation section to outside of the housing via a wireless or wired communication line.

12. The urine component analysis device according to claim 1,
wherein the specific component is one of sodium, potassium, calcium and glucose.

13. The urine component analysis device according to claim 1, wherein the urine component analysis device comprises an advice table which stores an excretion amount of salinity as the specific component in correspondence with an advice appropriate to the excretion amount of salinity for the subject; and
an advice section which selects an advice appropriate to the excretion amount of salinity as the specific component, which is calculated by the second calculation section, by referring to the advice table.

14. A urine component analysis method for determining an excretion amount of a specific component in total urine excreted by a subject in one day, the method comprising:
providing a urine component analysis device that comprises:
a housing;
a display section mounted and stored in the housing;
a sensor that is attached to the housing so as to project from one end of the housing; and
a non-transitory memory of a computer system, mounted in the housing, which stores data indicating a correlation between a concentration of the specific component in one urine excreted by a human and a concentration of the specific component in total urine in one day when all the urine excreted by the human in the one day is gathered into one volume;
acquiring, by a computer processor of the urine component analysis device a total amount of urine excreted by the subject in one day based on conversion or a database, and inputting data acquired by the sensor and indicating a concentration of the specific component in one urine excreted by the subject;

determining, by the computer processor, a concentration of the specific component in total urine in one day when all the urine excreted by the subject in the one day is gathered into one volume, by performing conversion using the correlation stored in the non-transitory memory, based on the input concentration of the specific component in the one urine of the subject, the computer processor being programmed with instructions for carrying out the determining;

calculating, by the computer processor, an excretion amount of the specific component in the total urine of the subject in the one day by multiplying the determined concentration of the specific component in the total urine in the one day by the total urine amount in the one day acquired based on conversion or a database, the computer processor also being programmed with instructions for carrying out the calculating; and displaying, by the display section mounted and stored in the housing of the urine component analysis device, a notification of the excretion amount of the calculated specific component.

* * * * *

UNITED STATES PATENT AND TRADEMARK OFFICE
CERTIFICATE OF CORRECTION

PATENT NO. : 9,506,906 B2
APPLICATION NO. : 14/173143
DATED : November 29, 2016
INVENTOR(S) : Hideyuki Yamashita et al.

It is certified that error appears in the above-identified patent and that said Letters Patent is hereby corrected as shown below:

On the Title Page

Item [71], Applicant, "OMRON HEALTHCARE Co., Ltd., Muko-shi, Kyoto (JP)", should read --OMRON HEALTHCARE CO., LTD., Kyoto (JP); OMRON CORPORATION, Kyoto (JP)--

Signed and Sealed this
Twenty-fifth Day of April, 2017

Michelle K. Lee
*Director of the United States Patent and Trademark Office*